United States Patent
Dalkara et al.

(10) Patent No.: US 11,723,988 B2
(45) Date of Patent: Aug. 15, 2023

(54) METHODS OF EXPRESSING A POLYNUCLEOTIDE OF INTEREST IN THE CONE PHOTORECEPTORS OF A SUBJECT COMPRISING THE SUBRETINAL DELIVERY OF A THERAPEUTICALLY EFFECTIVE AMOUNT OF A RECOMBINANT AAV9-DERIVED VECTOR

(71) Applicants: INSERM (INSTITUT NATIONAL DE LA SANTÉ ET DE LA RECHERCHE MÉDICALE), Paris (FR); SORBONNE UNIVERSITÉ, Paris (FR)

(72) Inventors: Deniz Dalkara, Alfortville (FR); Hanen Khabou, Noisy-le-Grand (FR); José-Alain Sahel, Paris (FR); Thierry Leveillard, Maison-Alfort (FR); Jens Duebel, Paris (FR)

(73) Assignees: INSERM (INSTITUT NATIONAL DE LA SANTÉ ET DE LA RECHERCHE MÉDICALE), Paris (FR); SORBONNE UNIVERSITE, Paris (FR)

( * ) Notice: Subject to any disclaimer, the term of this patent is extended or adjusted under 35 U.S.C. 154(b) by 397 days.

(21) Appl. No.: 16/756,988

(22) PCT Filed: Oct. 22, 2018

(86) PCT No.: PCT/EP2018/078856
§ 371 (c)(1),
(2) Date: Apr. 17, 2020

(87) PCT Pub. No.: WO2019/077159
PCT Pub. Date: Apr. 25, 2019

(65) Prior Publication Data
US 2021/0268125 A1    Sep. 2, 2021

(30) Foreign Application Priority Data
Oct. 20, 2017  (EP) ................................ 17306430

(51) Int. Cl.
*A61K 48/00* (2006.01)
*A61P 27/02* (2006.01)
*C12N 15/86* (2006.01)

(52) U.S. Cl.
CPC ...... *A61K 48/0058* (2013.01); *A61K 48/0075* (2013.01); *A61P 27/02* (2018.01); *C12N 15/86* (2013.01); *C12N 2750/14122* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | |
|---|---|---|
| 10,982,228 B2 | 4/2021 | Scaria et al. |
| 2014/0294771 A1 | 10/2014 | Schaffer et al. |
| 2015/0259395 A1 | 9/2015 | Chalberg et al. |
| 2016/0340661 A1 | 11/2016 | Cong et al. |
| 2016/0369299 A1 | 12/2016 | Boye et al. |
| 2017/0049910 A1* | 2/2017 | Cronin ............... A61K 48/0075 |

FOREIGN PATENT DOCUMENTS

| | | | |
|---|---|---|---|
| CN | 106661591 | 5/2017 | |
| WO | WO 2012/145601 | 10/2012 | |
| WO | WO 2016/014353 | 1/2016 | |
| WO | WO 2016/141078 | 9/2016 | |
| WO | WO-2017197355 A2 * | 11/2017 | ........... A61K 39/235 |
| WO | WO 2018/156654 | 8/2018 | |
| WO | WO 2019/076856 | 4/2019 | |

OTHER PUBLICATIONS

Khabou, H. et al. "Insight Into the Mechanisms of Enhanced Retinal Transduction by the Engineered AAV2 Capsid Variant-7m8" *Biotechnology and Bioengineering*, published online Jun. 30, 2016, pp. 2712-2724, vol. 113, No. 12.
Khabou, H. et al. "Noninvasive gene delivery to foveal cones for vision restoration" *JCI Insight*, Jan. 25, 2018, pp. 1-19, vol. 3, No. 2, e96029.
Schön, C. et al. "Retinal gene delivery by adeno-associated virus (AAV) vectors: Strategies and applications" *European Journal of Pharmaceutics and Biopharmaceutics*, 2015, pp. 1-10, vol. 95.
Ye, G.-J. et al. "Safety and Biodistribution Evaluation in CNGB3-Deficient Mice of rAAV2tYF-PR1.7-hCNGB3, a Recombinant AAV Vector for Treatment of Achromatopsia" *Human Gene Therapy Clinical Development*, Mar. 4, 2016, pp. 27-36, vol. 27, No. 1.
Written Opinion in International Application No. PCT/EP2018/078856, dated Feb. 5, 2019, pp. 1-6.
Investigative Ophthalmology and Visual Science, 2015, vol. 56, No. 7, pp. 1-2, STN [Online], [retrieved on Sep. 20, 2022], Accession No. 0052551616.

(Continued)

*Primary Examiner* — Brian Whiteman
(74) *Attorney, Agent, or Firm* — Saliwanchik, Lloyd & Eisenschenk

(57) ABSTRACT

Several new vector-promoter combinations to overcome the limitations associated with AAV-mediated cone transduction in the fovea are provided. The delivery modality relies on a cone-specific promoter and result in high-level transgene expression compatible with optogenetic vision restoration. Methods of expressing a polynucleotide of interest in the cone photoreceptors of a subject comprising subretinal delivery of a therapeutically effective amount of a recombinant AAV9-derived vector comprising a VP1 capsid protein as set forth in SEQ ID NO: 11 and the polynucleotide of interest under the control of the pR1.7 promoter as set forth in SEQ ID NO: 12 are also provided.

7 Claims, 5 Drawing Sheets
Specification includes a Sequence Listing.

(56) References Cited

OTHER PUBLICATIONS

Ye, G.-J. et al. "Cone-Specific Promoters for Gene Therapy of Achromatopsia and Other Retinal Diseases" *Human Gene Therapy*, 2016, pp. 72-82, vol. 27, No. 1.

Chuong, A. S. et al. "Noninvasive optical inhibition with a red-shifted microbial rhodopsin" *Nat Neurosci*. Aug. 2014, pp. 1-28, vol. 17, No. 8.

Vandenberghe, L. H. et al. "AAV9 Targets Cone Photoreceptors in the Nonhuman Primate Retina" *PLoS ONE*, Jan. 2013, pp. 1-7, vol. 8, Issue 1, e53463.

* cited by examiner

```
                         SEQUENCE LISTING

<160> NUMBER OF SEQ ID NOS: 15

<210> SEQ ID NO 1
<211> LENGTH: 7
<212> TYPE: PRT
<213> ORGANISM: Artificial Sequence
<220> FEATURE:
<223> OTHER INFORMATION: 7m8 peptide without spacer

<400> SEQUENCE: 1

Leu Gly Glu Thr Thr Arg Pro
1               5

<210> SEQ ID NO 2
<211> LENGTH: 7
<212> TYPE: PRT
<213> ORGANISM: Artificial Sequence
<220> FEATURE:
<223> OTHER INFORMATION: insertion peptide

<400> SEQUENCE: 2

Asn Glu Thr Ile Thr Arg Pro
1               5

<210> SEQ ID NO 3
<211> LENGTH: 7
<212> TYPE: PRT
<213> ORGANISM: Artificial Sequence
<220> FEATURE:
<223> OTHER INFORMATION: insertion peptide

<400> SEQUENCE: 3

Lys Ala Gly Gln Ala Asn Asn
1               5

<210> SEQ ID NO 4
<211> LENGTH: 7
<212> TYPE: PRT
<213> ORGANISM: Artificial Sequence
<220> FEATURE:
<223> OTHER INFORMATION: insertion peptide

<400> SEQUENCE: 4

Lys Asp Pro Lys Thr Thr Asn
1               5

<210> SEQ ID NO 5
<211> LENGTH: 7
<212> TYPE: PRT
<213> ORGANISM: Artificial Sequence
<220> FEATURE:
```

```
<223> OTHER INFORMATION: insertion peptide

<400> SEQUENCE: 5

Lys Asp Thr Asp Thr Thr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: insertion peptide

<400> SEQUENCE: 6

Arg Ala Gly Gly Ser Val Gly
1               5

<210> SEQ ID NO 7
<211> LENGTH: 7
<212> TYPE: PRT
<213> ORGANISM: Artificial Sequence
<220> FEATURE:
<223> OTHER INFORMATION: insertion peptide

<400> SEQUENCE: 7

Ala Val Asp Thr Thr Lys Phe
1               5

<210> SEQ ID NO 8
<211> LENGTH: 7
<212> TYPE: PRT
<213> ORGANISM: Artificial Sequence
<220> FEATURE:
<223> OTHER INFORMATION: insertion peptide

<400> SEQUENCE: 8

Ser Thr Gly Lys Val Pro Asn
1               5

<210> SEQ ID NO 9
<211> LENGTH: 10
<212> TYPE: PRT
<213> ORGANISM: Artificial Sequence
<220> FEATURE:
<223> OTHER INFORMATION: 7m8 peptide

<400> SEQUENCE: 9

Ala Ala Leu Gly Glu Thr Thr Arg Pro Ala
1               5                   10

<210> SEQ ID NO 10
<211> LENGTH: 733
<212> TYPE: PRT
<213> ORGANISM: adeno-associated virus 9

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60
```

-continued

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
             85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
```

```
                    485                 490                 495
Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Gln Ala Gln Thr
            580                 585                 590

Gly Trp Val Gln Asn Gln Gly Ile Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Met Lys
625                 630                 635                 640

His Pro Pro Pro Gln Ile Leu Ile Lys Asn Thr Pro Val Pro Ala Asp
                645                 650                 655

Pro Pro Thr Ala Phe Asn Lys Asp Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Asn Asn Val Glu Phe Ala Val Asn Thr Glu Gly Val Tyr
705                 710                 715                 720

Ser Glu Pro Arg Pro Ile Gly Thr Arg Tyr Leu Thr Arg
                725                 730

<210> SEQ ID NO 11
<211> LENGTH: 743
<212> TYPE: PRT
<213> ORGANISM: Artificial Sequence
<220> FEATURE:
<223> OTHER INFORMATION: VP1 capsid of the recombinant AAV9-derived
      vector

<400> SEQUENCE: 11

Met Ala Ala Asp Gly Tyr Leu Pro Asp Trp Leu Glu Asp Asn Leu Ser
1               5                  10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110
```

```
Asn Leu Gly Arg Ala Val Phe Gln Ala Lys Lys Arg Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
```

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Ala Leu Gly
        580                 585                 590

Glu Thr Thr Arg Pro Ala Gln Ala Gln Thr Gly Trp Val Gln Asn Gln
            595                 600                 605

Gly Ile Leu Pro Gly Met Val Trp Gln Asp Arg Asp Val Tyr Leu Gln
610                 615                 620

Gly Pro Ile Trp Ala Lys Ile Pro His Thr Asp Gly Asn Phe His Pro
625                 630                 635                 640

Ser Pro Leu Met Gly Gly Phe Gly Met Lys His Pro Pro Gln Ile
            645                 650                 655

Leu Ile Lys Asn Thr Pro Val Pro Ala Asp Pro Thr Ala Phe Asn
            660                 665                 670

Lys Asp Lys Leu Asn Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Tyr Lys Ser Asn Asn Val
705                 710                 715                 720

Glu Phe Ala Val Asn Thr Glu Gly Val Tyr Ser Glu Pro Arg Pro Ile
            725                 730                 735

Gly Thr Arg Tyr Leu Thr Arg
            740

<210> SEQ ID NO 12
<211> LENGTH: 1724
<212> TYPE: DNA
<213> ORGANISM: Artificial Sequence
<220> FEATURE:
<223> OTHER INFORMATION: pR1.7 promoter

<400> SEQUENCE: 12
ggaggctgag gggtggggaa agggcatggg tgtttcatga ggacagagct tccgtttcat      60
gcaatgaaaa gagtttggag acggatggtg gtgactggac tatacactta cacacggtag     120
cgatggtaca ctttgtatta tgtatatttt accacgatct ttttaaagtg tcaaaggcaa     180
atggccaaat ggttccttgt cctatagctg tagcagccat cggctgttag tgacaaagcc     240
cctgagtcaa gatgacagca gccccataa ctcctaatcg gctctcccgc gtggagtcat      300
ttaggagtag tcgcattaga gacaagtcca acatctaatc ttccaccctg ccagggccc      360 cagctggcag cgagggtggg agactccggg cagagcagag ggcgctgaca ttggggcccg     420
gcctggcttg ggtccctctg ccttttcccc aggggccctc tttccttggg gctttcttgg     480
gccgccactg ctcccgctcc tctccccca tcccacccc tcaccccctc gttcttcata      540
tccttctcta gtgctccctc cactttcatc caccttctg caagagtgtg ggaccacaaa     600
tgagttttca cctggcctgg ggacacacgt gccccacag gtgctgagtg actttctagg     660
acagtaatct gctttaggct aaaatgggac ttgatcttct gttagcccta atcatcaatt     720
agcagagccg gtgaaggtgc agaacctacc gcctttccag gcctcctccc acctctgcca     780
cctccactct ccttcctggg atgtgggggc tggcacacgt gtggcccagg gcattggtgg     840

```
gattgcactg agctgggtca ttagcgtaat cctggacaag ggcagacagg gcgagcggag      900
ggccagctcc ggggctcagg caaggctggg ggcttccccc agacacccca ctcctcctct      960
gctggacccc cacttcatag ggcacttcgt gttctcaaag ggcttccaaa tagcatggtg     1020
gccttggatg cccagggaag cctcagagtt gcttatctcc ctctagacag aaggggaatc     1080
tcggtcaaga gggagaggtc gccctgttca aggccaccca gccagctcat ggcggtaatg     1140
ggacaaggct ggccagccat cccacccctca gaagggaccc ggtggggcag gtgatctcag     1200
aggaggctca cttctgggtc tcacattctt ggatccggtt ccaggcctcg ccctaaaata     1260
gtctccctgg gctttcaaga gaaccacatg agaaaggagg attcgggctc tgagcagttt     1320
caccacccac cccccagtct gcaaatcctg acccgtgggt ccacctgccc caaaggcgga     1380
cgcaggacag tagaagggaa cagagaacac ataaacacag agagggccac agcggctccc     1440
acagtcaccg ccaccttcct ggcggggatg ggtggggcgt ctgagtttgg ttcccagcaa     1500
atccctctga gccgcccttg cgggctcgcc tcaggagcag gggagcaaga ggtggggagga     1560 ggaggtctaa gtcccaggcc caattaagag atcaggtagt gtagggtttg ggagctttta     1620
aggtgaagag gcccgggctg atcccacagg ccagtataaa gcgccgtgac cctcaggtga     1680
tgcgccaggg ccggctgccg tcgggacag ggctttccat agcc                       1724
```

<210> SEQ ID NO 13
<211> LENGTH: 552
<212> TYPE: PRT
<213> ORGANISM: Artificial Sequence
<220> FEATURE:
<223> OTHER INFORMATION: Jaws-GFP= Halo57 +2 mutations + KGC + GFP + ER2

<400> SEQUENCE: 13

```
Met Thr Ala Val Ser Thr Thr Ala Thr Thr Val Leu Gln Ala Thr Gln
 1               5                  10                  15

Ser Asp Val Leu Gln Glu Ile Gln Ser Asn Phe Leu Leu Asn Ser Ser
                20                  25                  30

Ile Trp Val Asn Ile Ala Leu Ala Gly Val Val Ile Leu Leu Phe Val
            35                  40                  45

Ala Met Gly Arg Asp Leu Glu Ser Pro Arg Ala Lys Leu Ile Trp Val
        50                  55                  60

Ala Thr Met Leu Val Pro Leu Val Ser Ile Ser Ser Tyr Ala Gly Leu
    65                  70                  75                  80

Ala Ser Gly Leu Thr Val Gly Phe Leu Gln Met Pro Pro Gly His Ala
                85                  90                  95

Leu Ala Gly Gln Glu Val Leu Ser Pro Trp Gly Arg Tyr Leu Thr Trp
            100                 105                 110

Thr Phe Ser Thr Pro Met Ile Leu Leu Ala Leu Gly Leu Leu Ala Asp
        115                 120                 125

Thr Asp Ile Ala Ser Leu Phe Thr Ala Ile Thr Met Asp Ile Gly Met
    130                 135                 140

Cys Val Thr Gly Leu Ala Ala Ala Leu Ile Thr Ser Ser His Leu Leu
145                 150                 155                 160

Arg Trp Val Phe Tyr Gly Ile Ser Cys Ala Phe Phe Val Ala Val Leu
                165                 170                 175

Tyr Val Leu Leu Val Gln Trp Pro Ala Asp Ala Glu Ala Ala Gly Thr
            180                 185                 190

Ser Glu Ile Phe Gly Thr Leu Arg Ile Leu Thr Val Val Leu Trp Leu
        195                 200                 205
```

Gly Tyr Pro Ile Leu Phe Ala Leu Gly Ser Glu Gly Val Ala Leu Leu
210                 215                 220

Ser Val Gly Val Thr Ser Trp Gly Tyr Ser Gly Leu Asp Ile Leu Ala
225                 230                 235                 240

Lys Tyr Val Phe Ala Phe Leu Leu Leu Arg Trp Val Ala Ala Asn Glu
                245                 250                 255

Gly Thr Val Ser Gly Ser Gly Met Gly Ile Gly Ser Gly Gly Ala Ala
            260                 265                 270

Pro Ala Asp Asp Arg Pro Val Val Lys Ser Arg Ile Thr Ser Glu Gly
        275                 280                 285

Glu Tyr Ile Pro Leu Asp Gln Ile Asp Ile Asn Val Ala Pro Ala Gly
    290                 295                 300

Ala Val Ser Lys Gly Glu Glu Leu Phe Thr Gly Val Val Pro Ile Leu
305                 310                 315                 320

Val Glu Leu Asp Gly Asp Val Asn Gly His Lys Phe Ser Val Ser Gly
                325                 330                 335

Glu Gly Glu Gly Asp Ala Thr Tyr Gly Lys Leu Thr Leu Lys Phe Ile
            340                 345                 350

Cys Thr Thr Gly Lys Leu Pro Val Pro Trp Pro Thr Leu Val Thr Thr
        355                 360                 365

Leu Thr Tyr Gly Val Gln Cys Phe Ser Arg Tyr Pro Asp His Met Lys
    370                 375                 380

Gln His Asp Phe Phe Lys Ser Ala Met Pro Glu Gly Tyr Val Gln Glu
385                 390                 395                 400

Arg Thr Ile Phe Phe Lys Asp Asp Gly Asn Tyr Lys Thr Arg Ala Glu
                405                 410                 415

Val Lys Phe Glu Gly Asp Thr Leu Val Asn Arg Ile Glu Leu Lys Gly
            420                 425                 430

Ile Asp Phe Lys Glu Asp Gly Asn Ile Leu Gly His Lys Leu Glu Tyr
        435                 440                 445

Asn Tyr Asn Ser His Asn Val Tyr Ile Met Ala Asp Lys Gln Lys Asn
    450                 455                 460

Gly Ile Lys Val Asn Phe Lys Ile Arg His Asn Ile Glu Asp Gly Ser
465                 470                 475                 480

Val Gln Leu Ala Asp His Tyr Gln Gln Asn Thr Pro Ile Gly Asp Gly
                485                 490                 495

Pro Val Leu Leu Pro Asp Asn His Tyr Leu Ser Thr Gln Ser Ala Leu
            500                 505                 510

Ser Lys Asp Pro Asn Glu Lys Arg Asp His Met Val Leu Leu Glu Phe
        515                 520                 525

Val Thr Ala Ala Gly Ile Thr Leu Gly Met Asp Glu Leu Tyr Lys Val
    530                 535                 540

Ala Phe Cys Tyr Glu Asn Glu Val
545                 550

<210> SEQ ID NO 14
<211> LENGTH: 300
<212> TYPE: PRT
<213> ORGANISM: Artificial Sequence
<220> FEATURE:
<223> OTHER INFORMATION: Jaws = Halo57 + 2 mutations + KGC + ER2

<400> SEQUENCE: 14

Met Thr Ala Val Ser Thr Thr Ala Thr Thr Val Leu Gln Ala Thr Gln
1               5                   10                  15

Ser Asp Val Leu Gln Glu Ile Gln Ser Asn Phe Leu Leu Asn Ser Ser
            20                  25                  30

Ile Trp Val Asn Ile Ala Leu Ala Gly Val Val Ile Leu Leu Phe Val
            35                  40                  45

Ala Met Gly Arg Asp Leu Glu Ser Pro Arg Ala Lys Leu Ile Trp Val
        50                  55                  60

Ala Thr Met Leu Val Pro Leu Val Ser Ile Ser Ser Tyr Ala Gly Leu
65                  70                  75                  80

Ala Ser Gly Leu Thr Val Gly Phe Leu Gln Met Pro Pro Gly His Ala
                85                  90                  95

Leu Ala Gly Gln Glu Val Leu Ser Pro Trp Gly Arg Tyr Leu Thr Trp
            100                 105                 110

Thr Phe Ser Thr Pro Met Ile Leu Leu Ala Leu Gly Leu Leu Ala Asp
            115                 120                 125

Thr Asp Ile Ala Ser Leu Phe Thr Ala Ile Thr Met Asp Ile Gly Met
130                 135                 140

Cys Val Thr Gly Leu Ala Ala Ala Leu Ile Thr Ser Ser His Leu Leu
145                 150                 155                 160

Arg Trp Val Phe Tyr Gly Ile Ser Cys Ala Phe Phe Val Ala Val Leu
                165                 170                 175

Tyr Val Leu Leu Val Gln Trp Pro Ala Asp Ala Glu Ala Ala Gly Thr
            180                 185                 190

Ser Glu Ile Phe Gly Thr Leu Arg Ile Leu Thr Val Val Leu Trp Leu
        195                 200                 205

Gly Tyr Pro Ile Leu Phe Ala Leu Gly Ser Glu Gly Val Ala Leu Leu
210                 215                 220

Ser Val Gly Val Thr Ser Trp Gly Tyr Ser Gly Leu Asp Ile Leu Ala
225                 230                 235                 240

Lys Tyr Val Phe Ala Phe Leu Leu Leu Arg Trp Val Ala Ala Asn Glu
                245                 250                 255

Gly Thr Val Ser Gly Ser Gly Met Gly Ile Gly Ser Gly Gly Ala Ala
            260                 265                 270

Pro Ala Asp Asp Arg Pro Val Val Lys Ser Arg Ile Thr Ser Glu Gly
        275                 280                 285

Glu Tyr Ile Pro Leu Asp Gln Ile Asp Ile Asn Val
290                 295                 300

<210> SEQ ID NO 15
<211> LENGTH: 300
<212> TYPE: PRT
<213> ORGANISM: Artificial Sequence
<220> FEATURE:
<223> OTHER INFORMATION: Halo57 + 2 mutations + KGC

<400> SEQUENCE: 15

Met Thr Ala Val Ser Thr Thr Ala Thr Thr Val Leu Gln Ala Thr Gln
1               5                   10                  15

Ser Asp Val Leu Gln Glu Ile Gln Ser Asn Phe Leu Leu Asn Ser Ser
            20                  25                  30

Ile Trp Val Asn Ile Ala Leu Ala Gly Val Val Ile Leu Leu Phe Val
            35                  40                  45

Ala Met Gly Arg Asp Leu Glu Ser Pro Arg Ala Lys Leu Ile Trp Val
        50                  55                  60

Ala Thr Met Leu Val Pro Leu Val Ser Ile Ser Ser Tyr Ala Gly Leu
65                  70                  75                  80

```
Ala Ser Gly Leu Thr Val Gly Phe Leu Gln Met Pro Pro Gly His Ala
                85              90              95
Leu Ala Gly Gln Glu Val Leu Ser Pro Trp Gly Arg Tyr Leu Thr Trp
            100             105             110
Thr Phe Ser Thr Pro Met Ile Leu Leu Ala Leu Gly Leu Leu Ala Asp
        115             120             125
Thr Asp Ile Ala Ser Leu Phe Thr Ala Ile Thr Met Asp Ile Gly Met
    130             135             140
Cys Val Thr Gly Leu Ala Ala Leu Ile Thr Ser Ser His Leu Leu
145             150             155             160
Arg Trp Val Phe Tyr Gly Ile Ser Cys Ala Phe Phe Val Ala Val Leu
            165             170             175
Tyr Val Leu Leu Val Gln Trp Pro Ala Asp Ala Glu Ala Ala Gly Thr
            180             185             190
Ser Glu Ile Phe Gly Thr Leu Arg Ile Leu Thr Val Val Leu Trp Leu
        195             200             205
Gly Tyr Pro Ile Leu Phe Ala Leu Gly Ser Glu Gly Val Ala Leu Leu
        210             215             220
Ser Val Gly Val Thr Ser Trp Gly Tyr Ser Gly Leu Asp Ile Leu Ala
225             230             235             240
Lys Tyr Val Phe Ala Phe Leu Leu Leu Arg Trp Val Ala Ala Asn Glu
            245             250             255
Gly Thr Val Ser Gly Ser Gly Met Gly Ile Gly Ser Gly Gly Ala Ala
            260             265             270
Pro Ala Asp Asp Arg Pro Val Val Lys Ser Arg Ile Thr Ser Glu Gly
            275             280             285
Glu Tyr Ile Pro Leu Asp Gln Ile Asp Ile Asn Val
    290             295             300
```

METHODS OF EXPRESSING A POLYNUCLEOTIDE OF INTEREST IN THE CONE PHOTORECEPTORS OF A SUBJECT COMPRISING THE SUBRETINAL DELIVERY OF A THERAPEUTICALLY EFFECTIVE AMOUNT OF A RECOMBINANT AAV9-DERIVED VECTOR

CROSS-REFERENCE TO RELATED APPLICATION

This application is the U.S. national stage application of International Patent Application No. PCT/EP2018/078856, filed Oct. 22, 2018.

The Sequence Listing for this application is labeled "Seq-List.txt" which was created on Apr. 9, 2020 and is 27 KB. The entire content of the sequence listing is incorporated herein by reference in its entirety.

FIELD OF THE INVENTION

The present invention relates to a recombinant AAV9-derived vector and to its applications, in particular a method of expressing a polynucleotide of interest in the cone photoreceptors of a subject comprising the subretinal delivery of a therapeutically effective amount of a recombinant AAV9-derived vector.

BACKGROUND OF THE INVENTION

The fovea—located at the center of the macula—is a specialized region of the retina that dominates the visual perception of primates by providing high acuity color vision (1). The highest density of cones is found at the center of the fovea (<0.3 mm from the foveal center), devoid of rod photoreceptors (2). Cone density decreases by up to 100 fold with distance from the fovea (3). Cone cells in the fovea are the primary targets of gene therapies aiming to treat inherited retinal diseases like mid-stage retinitis pigmentosa (4, 5) and achromatopsia (6). Currently, viral vectors encoding therapeutic proteins need to be injected into the subretinal space between the photoreceptors and the retinal pigmented epithelium (RPE) cells in order to provide gene delivery to cones. In this approach, gene delivery with conventional AAVs (i.e. AAV2) is limited to cells that contact the local "bleb" of injected fluid. Furthermore, retinal detachment that occurs during subretinal injections is a concern in eyes with retinal degeneration. The earliest clinical trials using subretinal delivery of adeno-associated virus (AAV) to deliver a healthy RPE65 gene in Leber's Congenital Amaurosis patients (7-9) lead to some improvements in vision despite the detachment of the macula to deliver the viral vector (10, 11). However, the treatment was in certain cases complicated by macular holes and increased macular thinning in the case of sub-foveal injections (11). Furthermore, contrary to the surrounding regions, there were no treatment benefits in the fovea (12). Gene therapy using AAV has also been studied for patients with choroideremia in which the macula was the target for gene delivery (13). The 6 month follow up results from this latter study thus far suggest that sub-foveal retinal detachment does not cause vision reduction in this region but, one of the patients in this trial had visual acuity loss in the treated eye compared to his untreated eye (13). With more gene therapies reaching clinical stages of application there is a growing need to find new methods for delivering gene therapy to the fovea without detaching this brittle region (14). This can be achieved by subretinal injections in the periphery using vectors that spread laterally to reach the foveal region.

SUMMARY OF THE INVENTION

The present invention relates to a recombinant AAV9-derived vector and to its applications, including a method of expressing a polynucleotide of interest in the cone photoreceptors of a subject comprising the subretinal delivery of a therapeutically effective amount of a recombinant AAV9-derived vector. In particular, the present invention is defined by the claims.

In a first aspect, the present invention relates to a recombinant AAV9-derived vector for use in the treatment of a retinal disease affecting cone photoreceptors, said vector comprising:
  a VP1 capsid protein in which a 7 to 11 amino-acid length peptide is inserted in the GH loop of said capsid protein relative to a corresponding wild-type AAV9 capsid protein, wherein said peptide comprises any one of SEQ ID NO: 1 to SEQ ID NO: 8; and
  a polynucleotide of interest under the control of the pR1.7 promoter as set forth in SEQ ID NO: 12 or of a functional variant of said promoter.

Preferably, the peptide is inserted in the GH loop between amino acids 588 and 589 relative to the wild-type AAV9 capsid protein as set forth in SEQ ID NO: 10.

Preferably, the peptide comprises or consists of SEQ ID NO: 9.

Preferably, the recombinant AAV9-derived vector comprises a VP1 capsid protein as set forth in SEQ ID NO:11 and a polynucleotide of interest under the control of the pR1.7 promoter as set forth in SEQ ID NO: 12.

Preferably, the subject to be treated by the recombinant AAV9-derived vector suffers from a retinal disease selected from the group consisting of age-related macular degeneration, Bassen-kornzweig syndrome, choroideremia, gyrate atrophy, Refsum syndrome, Usher syndrome, color blindness, blue cone monochromacy, achromatopsia, incomplete achromatopsia, oligocone trichromacy, retinitis pigmentosa (RP), macular degeneration, Stargardt's Disease, Bardet-Biedl syndrome, Bornholm eye disease, Best's Disease and Leber's congenital amaurosis.

Preferably, the polynucleotide of interest is a gene that can be used in gene replacement therapy, preferably selected from a gene encoding for retinitis pigmentosa GTPase regulator (RPGRORF15), CNGB3 (beta subunit of the cone cyclic nucleotide-gated cation channel), CNGA3 (alpha subunit of the cone cyclic nucleotide-gated cation channel) or GNAT2.

Preferably, the polynucleotide of interest encodes for a neurotrophic factor. More preferably, the polynucleotide of interest encodes for RdCVF, RdCVF2, RdCVFL or RdCVFL2.

Preferably, the polynucleotide of interest encodes for an opsin such as rhodopsin, photopsin, L/M wavelength (red/green) cone-opsin, or short wavelength (S) cone-opsin (blue). More preferably, the polynucleotide of interest encodes for an opsin consisting of an amino acid sequence as set forth in SEQ ID NO: 13, SEQ ID NO:14 or SEQ ID NO: 15.

Preferably, the polynucleotide of interest encodes for a site-specific endonuclease that provides for site-specific knock-down of gene function selected from the group consisting of zinc finger nucleases (ZFNs), transcription activator-like effector nucleases (TALENs), and CRISPR-associated endonucleases. More preferably, the polynucleotide of interest encodes for Cas9 nuclease.

Preferably, the polynucleotide of interest encodes for an interfering RNA (RNAi), in particular a siRNA or shRNA.

Preferably, the polynucleotide of interest encodes for an antisense oligonucleotide.

Preferably, the treatment comprises the subretinal delivery of a therapeutically effective amount of the recombinant AAV9-derived vector.

Preferably, the subretinal delivery is performed at distance of the fovea without detaching said region.

In another aspect, the invention relates to a recombinant AAV9-derived vector,
comprising:
  a VP1 capsid protein in which a 7 to 11 amino-acid length peptide is inserted in the GH loop of said capsid protein relative to a corresponding wild-type AAV9 capsid protein, wherein said peptide comprises any one of SEQ ID NO: 1 to SEQ ID NO: 8; and
  a polynucleotide of interest under the control of the pR1.7 promoter as set forth in SEQ ID NO: 12 or of a functional variant of said promoter.

Preferably, the peptide is as described above.

Preferably, the recombinant AAV9-derived vector comprises a VP1 capsid protein as set forth in SEQ ID NO:11 and a polynucleotide of interest under the control of the pR1.7 promoter as set forth in SEQ ID NO: 12.

Preferably, the polynucleotide of interest is as described above.

In another aspect, the invention relates to a method of expressing a polynucleotide of interest in the cone photoreceptors of a subject comprising the subretinal delivery of a therapeutically effective amount of the recombinant AAV9-derived vector.

DETAILED DESCRIPTION OF THE INVENTION

Gaps in our understanding of AAV transduction patterns within the anatomically unique environments of the subretinal space of the primate eye impeded the establishment of non-invasive and efficient gene delivery to foveal cones in the clinic. Here, the inventors establish several new vector-promoter combinations to overcome the limitations associated with AAV-mediated cone transduction in the fovea with supporting studies in mouse models, human induced pluripotent stem cell-derived organoids, post-mortem human retinal explants and living macaques. They show that an AAV9 variant provides efficient foveal cone transduction when injected into the subretinal space several millimeters away from the fovea, without detaching this delicate region. This delivery modality relies on a cone-specific promoter and results in high-level transgene expression compatible with optogenetic vision restoration.

Accordingly, the first object of the present invention relates to a recombinant AAV9-derived vector, comprising:
  a VP1 capsid protein in which a 7 to 11 amino-acid length peptide is inserted in the GH loop of said capsid protein relative to a corresponding wild-type AAV9 capsid protein, wherein said peptide comprises any one of SEQ ID NO: 1 to SEQ ID NO: 8; and
  a polynucleotide of interest under the control of the pR1.7 promoter as set forth in SEQ ID NO: 12 or of a functional variant of said promoter.

In particular, the recombinant AAV9-derived vector may comprise the VP1 capsid protein as set forth in SEQ ID NO:11 and a polynucleotide of interest under the control of the pR1.7 promoter as set forth in SEQ ID NO:12.

Another object of the present invention relates to a method of expressing a polynucleotide of interest in the cone photoreceptors of a subject comprising the subretinal delivery of a therapeutically effective amount of the recombinant AAV9-derived vector according to the invention.

As used herein, the term "subject" is typically intended for a human. Typically, the subject is affected or likely to be affected with a retinal disease affecting cone photoreceptors. Such retinal disease can affect directly or indirectly the cone photoreceptors. Accordingly, a wide variety of retinal diseases impacting retinal cone photoreceptors may thus be treated given the teachings provided herein and typically include age-related macular degeneration, Bassen-kornzweig syndrome, choroideremia, gyrate atrophy, Refsum syndrome, Usher syndrome, color blindness, blue cone monochromacy, achromatopsia, incomplete achromatopsia, oligocone trichromacy, retinitis pigmentosa (RP), macular degeneration, Stargardt's Disease, Bardet-Biedl syndrome, Bornholm eye disease, Best's Disease and Leber's congenital amaurosis.

Accordingly, a further object of this invention is to provide a method for treating a retinal disease affecting cone photoreceptors in a subject in need thereof comprising the subretinal delivery of a therapeutically effective amount of the recombinant AAV9-derived vector according to the invention. In this aspect, when expressed in cone photoreceptors, the polynucleotide of interest, in particular under the control of the pR1.7 promoter as set forth in SEQ ID NO: 12, has a beneficial effect on the retinal disease, in particular is capable of treating said disease.

The present invention also relates to the recombinant AAV9-derived vector according to the invention, for use in the treatment of a retinal disease affecting cone photoreceptors. In particular, the present invention relates to the use of said recombinant AAV9-derived vector, for the preparation of a medicament for the treatment of a retinal disease affecting cone photoreceptors. As explained above, preferably, the treatment comprises the subretinal delivery of a therapeutically effective amount of the recombinant AAV9-derived vector, and the polynucleotide of interest is capable of treating the retinal disease.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "cone photoreceptors" has its general meaning in the art and are one of three types of photoreceptor cells in the retina of mammalian eyes. They are responsible for color vision and function best in relatively bright light, as opposed to rod cells, which work better in dim light. The combination between the specific vector and the pR1.7 promoter (or functional variant of said promoter) specially drives the expression of the polynucleotide of interest in cone photoreceptors.

As used herein, the term "subretinal delivery" refers to the administration of the vector into the subretinal space, which refers to the location in the retina between the photoreceptor cells and the retinal pigment epithelium cells. The subretinal delivery leads to the formation of a "bleb", which refers to a fluid-filled pocket within the subretinal space of an eye. A bleb of the invention may be created by a single injection of fluid into a single space, by multiple injections of one or more fluids into the same space, or by multiple injections into multiple spaces, which when repositioned create a total fluid space useful for achieving a therapeutic effect over the desired portion of the subretinal space.

According to the present invention, the subretinal delivery is performed at distance of the fovea, which means that the bleb is formed greater than or equal to 0.5 millimeters away from the center of the fovea, without detaching this delicate region. As used herein, the term "fovea" has its general meaning in the art and refers to a small region in the central retina of primates of approximately equal to or less than 0.5 mm in diameter that contains only cone photoreceptor cells, and highest density of cones in the whole retina.

As used herein, the term "polynucleotide of interest" herein designates any nucleotide sequence coding for any polypeptide, structural protein, enzyme etc., the expression of which is wanted in a target cell, for any kind of reason. It can also designate a non-coding sequence, for example an antisense sequence or the sequence of an interfering RNA aimed at decreasing the expression of a gene. One skilled in the art knows, by its knowledge of the scientific literature in his field, which are the polynucleotides that may be more appropriate to treat a specific retinal disease.

Gene therapy can be performed either by introducing in cone photoreceptor a functional copy of a polynucleotide of interest (e.g. a gene) that is deficient therein (gene replacement therapy), or by delivering to cone photoreceptors a polynucleotide of interest which will have a beneficial effect on the eye disease to be treated (symptomatic therapy). In other words, the polynucleotide of interest is preferably capable of treating a retinal disease affecting cone photoreceptors. Examples of polynucleotides of interest that can be used for gene replacement therapy are genes that are specifically or preferentially expressed in cone photoreceptors, such as retinitis pigmentosa GTPase regulator (RPGRORF15) (refs: 1. B. S. Pawlyk, O. V. Bulgakov, X. Sun, M. Adamian, X. Shu, A. J. Smith, E. L. Berson, R. R. Ali, S. Khani, A. F. Wright, M. A. Sandberg, T. Li, Photoreceptor rescue by an abbreviated human RPGR gene in a murine model of X-linked retinitis pigmentosa. Gene Ther 23, 196-204 (2016); 2. D. H. Hong, B. S. Pawlyk, M. Adamian, M. A. Sandberg, T. Li, A single, abbreviated RPGR-ORF15 variant reconstitutes RPGR function in vivo. Invest Ophthalmol Vis Sci 46, 435-441 (2005); 3. W. A. Beltran, A. V. Cideciyan, A. S. Lewin, W. W. Hauswirth, S. G. Jacobson, G. D. Aguirre, Gene augmentation for X-linked retinitis pigmentosa caused by mutations in RPGR. Cold Spring Harbor perspectives in medicine 5, a017392 (2014); 4. W. T. Deng, F. M. Dyka, A. Dinculescu, J. Li, P. Zhu, V. A. Chiodo, S. L. Boye, T. J. Conlon, K. Erger, T. Cossette, W. W. Hauswirth, Stability and Safety of an AAV Vector for Treating RPGR-ORF15 X-Linked Retinitis Pigmentosa. Hum Gene Ther 26, 593-602 (2015). 5. Z. Wu, S. Hiriyanna, H. Qian, S. Mookherjee, M. M. Campos, C. Gao, R. Fariss, P. A. Sieving, T. Li, P. Colosi, A. Swaroop, A long-term efficacy study of gene replacement therapy for RPGR-associated retinal degeneration. Hum Mol Genet 24, 3956-3970 (2015); 6. W. A. Beltran, A. V. Cideciyan, A. S. Lewin, S. Iwabe, H. Khanna, A. Sumaroka, V. A. Chiodo, D. S. Fajardo, A. J. Roman, W.-T. Deng, M. Swider, T. S. Alemán, S. L. Boye, S. Genini, A. Swaroop, W. W. Hauswirth, S. G. Jacobson, G. D. Aguirre, in Proc. Natl. Acad. Sci. U.S.A. (2012), vol. 109, pp. 2132-2137), CNGB3 (beta subunit of the cone cyclic nucleotide-gated cation channel) (see, e.g., Kohl et al. (2005) Eur J Hum Genet. 13(3):302), GNAT2 (cone specific alpha subunit of transducin) and CNGA3 (alpha subunit of the cone cyclic nucleotide-gated cation channel) (see, e.g., GenBank Accession No. NP_001289; and Booij et al. (2011) Ophthalmology 118: 160-167).

In some embodiments, the polynucleotide of interest may encode for a neurotrophic factor. As used herein, the "neurotrophic factor" is a generic term of proteins having a physiological action such as survival and maintenance of nerve cells, promotion of neuronal differentiation. In some embodiments, the neurotrophic factor is RdCVF. As used herein the term "RdCVF" has its general meaning in the art and refers to rod-derived cone viability factor (Léveillard T, Mohand-Said S, Lorentz O, Hicks D, Fintz A C, Clérin E et al. Identification and characterization of rod-derived cone viability factor. Nat Genet 2004; 36: 755-759). The gene encodes both a long form (RdCVF-L, 217 aa, Q8VC33) having a putative thiol-oxydoreductase activity (JEFFERY, Trends Biochem. Sci., vol. 24(1):8-11, 1999; JEFFERY, Trends Genet., vol. 19(8):415-417, 2003) and a short form (RdCVF-S, 109 aa, Q91W38) with trophic activity for cones but no redox activity. In some embodiments, the neurotrophic factor is RdCVF2, which shares many similarities with RdCVF in terms of gene structure, expression in a rod-dependent manner and protein 3D structure (see e.g. WO2008148860 and Chalmel F, Léveillard T, Jaillard C, Lardenois A, Berdugo N, Morel E, Koehl P, Lambrou G, Holmgren A, Sahel J A, Poch O. Rod-derived Cone Viability Factor-2 is a novel bifunctional-thioredoxin-like protein with therapeutic potential. BMC Mol Biol. 2007 Aug. 31; 8:74). Like RdCVF, the RdCVF2 short isoform exhibits cone rescue activity that is independent of its putative thiol-oxydoreductase activity. In some embodiments, the polynucleotide of interest encodes for RdCVFL2.

In some embodiments, the polynucleotide product of interest is an opsin. The opsin sequence can be derived from any suitable single- or multicellular-organism, including human, algae and bacteria. In some embodiments, the opsin is rhodopsin, photopsin, L/M wavelength (red/green) cone-opsin, or short wavelength (S) cone-opsin (blue). In some embodiments, the opsin is channelrhodopsin or halorhodopsin or cruxhalorhodopsin. In some embodiments, the opsin is a light-responsive opsin as described in U.S. Patent Publication No. 2007/0261127 (e.g., ChR2; Chop2); U.S. Patent Publication No. 2001/0086421; U.S. Patent Publication No. 2010/0015095; and Diester et al. (2011) Nat. Neurosci. 14:387. Other examples of opsins include NpHR, eNpHR 1.0, eNpHR 2.0, eNpHR 3.0, SwiChR, SwiChR 2.0, SwiChR 3.0, Mac, Mac 3.0, Arch, ArchT, Arch 3.0, ArchT 3.0, iChR, ChR2, C1V1-T, C1V1-TT, Chronos, Chrimson, ChrimsonR, CatCh, VChR1-SFO, ChR2-SFO, ChR2-SSFO, ChEF, ChIEF, Jaws, ChloC, Slow ChloC, iC1C2, iC1C2 2.0, and iC1C2 3.0. In some embodiments, the opsin consists of the amino acid sequence as set forth in SEQ ID NO: 13 or SEQ ID NO: 14, or SEQ ID NO: 15.

In some embodiments, the polynucleotide product of interest is a site-specific endonuclease that provides for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease can be targeted to the defective allele and knock out the defective allele. In some embodiments, the vector thus comprises a polynucleotide that encodes a site-specific endonuclease; and a polynucleotide that encodes a functional copy of a defective allele, where the functional copy encodes a functional retinal protein. Site-specific endonucleases that are suitable for use include, e.g., zinc finger nucleases (ZFNs); transcription activator-like effector nucleases (TALENs), and CRISPR-associated endonuclease. As used herein, the term "CRISPR-associated endonuclease" has its general meaning in the art and refers to clustered regularly interspaced short palindromic repeats associated which are the segments of prokaryotic DNA containing short repetitions of base sequences. As well-known in the art, a CRISPR-associated endonuclease can be associated with a small guide RNA (gRNA) and/or homology-directed repair (HDR) template. In particular, the CRISPR-associated endonuclease according to the invention is Cas9 or a derivative thereof. The Cas9 nuclease can have a nucleotide sequence identical to the wild type *Streptococcus pyrogenes* or *Staphylococcus aureus* sequence, preferably to the wild type *Streptococcus pyrogenes*. Alternatively, the wild type *Streptococcus pyrogenes* or *Staphylococcus aureus* Cas9 sequence can be modified. For instance, the Cas9 nuclease sequence can be, the sequence contained within a commercially available vector such as PX330 or PX260 from Addgene (Cambridge, Mass.). In some embodiments, the Cas9 endonuclease can have an amino acid sequence that is a variant or a fragment of any of the Cas9 endonuclease sequences of Genbank accession numbers KM099231.1 GL669193757; KM099232.1; GL669193761; CP032481; LT996890; CP031130; CP022607; AP014942 or KM099233.1 GL669193765 or Cas9 amino acid sequence of PX330 or PX260 (Addgene, Cambridge, Mass.). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). For example, the Cas9 nuclease can be mutated in the conserved FiNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks. In some embodiments, the vector comprises one or more guide RNA. As used herein, the term "one or more guide RNA" refers to the RNAs that guide the insertion or deletion of residues. In the context of the invention, the guide RNA is used for recruiting Cas9 to specific genomic loci. In some embodiments, the guide RNA can be a sequence complementary to a coding or a non-coding sequence. In some embodiments, the subject is administered with a combination of at least one vector comprising one polynucleotide encoding for a Cas9 endonuclease and at least one vector comprising the guide RNA.

In some embodiments, the polynucleotide product is an interfering RNA (RNAi), in particular a siRNA. A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides.

In some embodiment, the polynucleotide product is short hairpin RNA (shRNA). The term "short hairpin" or shRNA refers to a RNA which contains nucleotides in a loop structure, and which is processed to siRNA. An shRNA thus also leads to the know-down of a gene in a sequence-specific manner dependent upon complimentary binding of the target gene.

In some embodiments, the polynucleotide product is an antisense oligonucleotide. As used herein, the term "antisense oligonucleotide" is understood to refer to a nucleotide sequence which is substantially complementary to a target nucleotide sequence in a pre-mRNA molecule, hnRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

As used herein the term "AAV" refers to the more than 30 naturally occurring and available adeno-associated viruses, as well as artificial AAVs. Typically, the AAV capsid, ITRs, and other selected AAV components described herein, may be readily selected from among any AAV, including, without limitation, AAV1, AAV2, AAV3, AAV4, AAV5, AAV6, AAV6.2, AAV7, AAV8, AAV9, rh10, AAVrh64R1, AAVrh64R2, rh8, variants of any of the known or mentioned AAVs or AAVs yet to be discovered or variants or mixtures thereof. See, e.g., WO 2005/033321. The genomic and proteic sequences of various serotypes of AAV, as well as the sequences of the native terminal repeats (TRs), Rep proteins, and capsid subunits including VP1 protein are known in the art. Such sequences may be found in the literature or in public databases such as GenBank or Protein Data Bank (PDB). See, e.g., GenBank and PDB Accession Numbers NC_002077 and 3NG9 (AAV-1), AF043303 and 1LP3 (AAV-2), NC_001729 (AAV-3), U89790 and 2G8G (AAV-4), NC_006152 and 3NTT (AAV-5), 3OAH (AAV6), AF513851 (AAV-7), NC_006261 and 2QA0 (AAV-8), AY530579 and 3UX1 (AAV-9 (isolate hu.14)); the disclosures of which are incorporated by reference herein for teaching AAV nucleic acid and amino acid sequences. See also, e.g., Srivistava et al. (1983) J. Virology 45:555; Chiorini et al. (1998) J. Virology 71:6823; Chiorini et al. (1999) J. Virology 73: 1309; Bantel-Schaal et al. (1999) J. Virology 73:939; Xiao et al. (1999) J. Virology 73:3994; Muramatsu et al. (1996) Virology 221:208; Shade et al. (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. Nos. 6,156,303 and 7,906,111.

As used herein, the term "recombinant AAV9-derived vector" or "rAAV9-derived vector" refers to an adeno-associated virus type 9, comprising a polynucleotide sequence of interest that is not of AAV9 origin (i.e. heterologous sequence, such as a transgene to be delivered to a cell) and/or of which the natural DNA or protein(s) (Cap and/or Rep) has been modified, for example to alter its tropism. In other words, said rAAV9-derived vector is not naturally-occurring. In the context of the present invention, the rAAV9-derived vector comprises the polynucleotide sequence of interest described above (as an heterologous sequence) under the control of a specific promoter, as well as a modified AAV9 VP1 capsid protein, so as to provide efficient delivery and high-level expression of the polynucleotide into cone photoreceptors, preferably upon subretinal injection, while minimizing any potential side-effects such as the development of neutralizing antibodies against the vector and/or off-target expression in neighboring cells.

More particularly, the recombinant AAV9-derived vector according to the invention comprises:
a VP1 capsid protein in which a 7 to 11 amino-acid length peptide is inserted in the GH loop of said capsid protein relative to a corresponding wild-type AAV9 capsid protein, wherein said peptide comprises any one of SEQ ID NO: 1 to SEQ ID NO: 8; and
a polynucleotide of interest under the control of the pR1.7 promoter as set forth in SEQ ID NO: 12 or of a functional variant of said promoter.

As noted above, a peptide of 7 to 11 amino acids in length and comprising any one of SEQ ID NO: 1 to SEQ ID NO: 8 (also called herein insertion peptide) is inserted in the GH loop of the VP1 capsid protein. This means that said insertion peptide can have a length of 7 amino acids, 8 amino acids, 9 amino acids, 10 amino acids or 11 amino acids. More particularly, the insertion peptide can have a spacer at the amino-terminus and/or at the carboxyl terminus of any one of SEQ ID NO: 1 to SEQ ID NO: 8. Suitable spacers according to the invention include, but are not limited to, one or more leucine, alanine, glycine and serine. For example, the insertion peptide according to the invention preferably comprises or consists of SEQ ID NO: 9. More preferably, the insertion peptide according to the invention consists of SEQ ID NO: 9. The role of the insertion peptide is to increase the rAAV9-vector infectivity into cone photoreceptors compared to a wild-type AAV9.

Because of the presence of this insertion peptide, the VP1 capsid protein of the rAAV9-vector is said to be modified relative to a wild-type (i.e. native) AAV9 capsid protein (such as SEQ ID NO: 10). Optionally, the VP1 capsid protein according to the invention can comprise further modifications (i.e. mutations), such as an amino acid deletion, an amino acid substitution or a further amino acid insertion, as long as said capsid protein retains its capacity to encapsulate the polynucleotide of interest and to bind to the target cell of interest, internalize and traffic within said cell. Methods allowing introduction of such mutations are known to the skilled person in the art. For example, it is possible to introduce a mutation by random or directed mutagenesis, by PCR using degenerate primers, e.g. in the nucleotide sequence coding for a protein of reference. Said techniques are notably described by Sambrook et al. in "Molecular Cloning: A laboratory Manual", 4th edition, Cold Spring Harbor Laboratory Press, (2012, and updates from 2014), and by Ausubel et al. in "Current 25 Protocols in Molecular Biology", John Wiley & Sons (2012).

The peptide insertion occurs within the GH loop (also known as loop IV) of said capsid protein, more particularly, in a solvent-accessible region of the GH loop (Van Vliet et al. (2006) Mol. Ther. 14:809; Padron et al. (2005) J. Virol. 79:5047; and Shen et al. (2007) Mol. Ther. 15: 1955). In a preferred embodiment, the insertion site of said peptide is a single insertion site between two adjacent amino acids located between amino acids 570-614 of AAV9 capsid protein. For example, the insertion site is within amino acids 571 to 612 of AAV9 capsid protein. More preferably, the insertion site of said peptide is located between amino acids 588 and 589 of AAV9 capsid protein.

Accordingly, in a preferred embodiment, the peptide as described above is inserted in the GH loop between amino acids 588 and 589 relative to the wild-type AAV9 capsid protein as set forth in SEQ ID NO: 10.

In a more preferred embodiment, the peptide as described above is inserted in the GH loop between amino acids 588 and 589 of the wild-type AAV9 capsid protein as set forth in SEQ ID NO: 10.

Even more preferably, the peptide comprising SEQ ID NO: 1, preferably the peptide of SEQ ID NO: 9, is inserted in the GH loop between amino acids 588 and 589 of the wild-type AAV9 capsid protein as set forth in SEQ ID NO: 10. In other words, the rAAV9 vector according to the invention most preferably comprises the VP1 capsid protein as set forth in SEQ ID NO: 11 and the polynucleotide sequence of interest (i.e., a polynucleotide heterologous to AAV). Thus, in the recombinant AAV9-derived vector of the present invention, the native VP1 capsid protein of AAV9 as set forth in SEQ ID NO: 10 may be substituted by the VP1 capsid protein as set forth in SEQ ID NO: 11.

The recombinant AAV9-derived vector of the present invention typically comprises 5' and 3' adeno-associated virus inverted terminal repeats (ITRs), the polynucleotide of interest (i.e. a heterologous polynucleotide) operatively linked to the promoter pR1.7. For the purpose of the present invention, the polynucleotide of interest, operatively linked to the promoter pR1.7, is preferably flanked by two AAV ITRs. The vectors of the invention are produced using methods known in the art. In short, the methods generally involve (a) the introduction of the AAV vector into a host cell, (b) the introduction of an AAV helper construct into the host cell, wherein the helper construct comprises the viral functions missing from the AAV vector and (c) introducing a helper virus into the host cell. All functions for AAV virion replication and packaging need to be present, to achieve replication and packaging of the AAV vector into AAV virions. The introduction into the host cell can be carried out using standard virology techniques simultaneously or sequentially. Finally, the host cells are cultured to produce AAV virions and are purified using standard techniques such as iodixanol or CsCl gradients or other purification methods. The purified AAV virion is then ready for use in the methods.

As used herein, the term "promoter" has its general meaning in the art and refers to a nucleic acid fragment that controls the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. As used herein, the term "pR1.7 promoter" refers to the 1.7-kb L-opsin promoter described in Hum Gene Ther. 2016 January; 27(1):72-82 and characterized by the nucleic acid sequence as set forth in SEQ ID NO: 12. The promoter and the polynucleotide of interest are operatively linked. As used herein, the term "operably linked" refers to two or more nucleic acid or amino acid sequence elements that are physically linked in such a way that they are in a functional relationship with each other. For instance, a promoter is operably linked to a coding sequence if the promoter is able to initiate or otherwise control/regulate the transcription and/or expression of a coding sequence, in which case the coding sequence should be understood as being "under the control of" the promoter. Generally, when two nucleic acid sequences are operably linked, they will be in the same orientation and usually also in the same reading frame. They will usually also be essentially contiguous, although this may not be required.

The present invention further encompasses rAAV9-derived vectors as described herein, in which the polynucleotide of interest is under the control of a functional variant of the pR7.1 promoter. "Functional variants" of the pR7.1 promoter typically have one or more nucleotide mutations (such as a nucleotide deletion, addition, and/or substitution) relative to the native pR7.1 promoter (SEQ ID NO: 12), which do not significantly alter the transcription of the polynucleotide of interest. In the context of the present invention, said functional variants retain the capacity to drive a strong expression, in cone photoreceptors, of the polynucleotide of interest. Such capacity can be tested as described by Ye et al. (2016) (18) and Khabou et al. (2018) (17).

In a preferred embodiment, the polynucleotide of interest is under the control of the pR1.7 promoter as set forth in SEQ ID NO: 12 or of a functional variant of said promoter having at least 70%, preferably at least 75%, 80%, 85%, 90%, 95% or 99% sequence identity thereto.

As well-known to the skilled practitioner, the "% of sequence identity" between two nucleotide (or amino acid) sequences is a function of the number of identical positions shared by the sequences, upon alignment for optimal comparison. When a position in the compared sequences is occupied by the same nucleotide (or amino acid), the sequences are said to be identical at that position. Indeed, identity only refers to perfect matches, and does not consider the degree of similarity of nucleotide (or amino acids) to one another. The percentage of sequence identity can be calculated by multiplying the number of identical positions by 100 and dividing by the length of the aligned region (overlapping positions), including gaps (only internal gaps, not the gaps at the sequence ends). In this comparison, the sequences can be of the same length, or may be of different lengths. Optimal alignment of sequences may be herein preferably conducted by a global homology alignment algorithm should the alignment be performed using sequences of the same or similar length, such as by the algorithm described by Needleman and Wunsch (Journal of Molecular Biology; 1970, 48(3): 443-53), by computerized implementations of this algorithm (e.g., using the DNASTAR® Lasergene software), or by visual inspection. Alternatively, should the alignment be performed using sequences of distinct length, the optimal alignment of sequences can be preferably conducted by a local homology alignment algorithm, such as by the algorithm described by Smith and Waterson (Journal of Molecular Biology; 1981, 147: 195-197), by computerized implementations of this algorithm (e.g., using the DNASTAR® Lasergene software), or by visual inspection. Examples of global and local homology alignment algorithms are well-known to the skilled practitioner, and include, without limitation, ClustalV (global alignment), ClustalW (local alignment) and BLAST (local alignment).

By "therapeutically effective amount", it is meant a sufficient amount of the vector to treat the retinal disease at a reasonable benefit/risk ratio. It will be understood that the total daily usage of the vector will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. Thus, the doses of vectors may be adapted depending on the disease condition, the subject (for example, according to the subject's weight and/or age, metabolism, state of the retina, etc.), the treatment schedule, etc. A preferred effective dose within the context of this invention is a dose allowing an optimal transduction of the cone photoreceptors. Typically, from $10^8$ to $10^{10}$ viral genomes (vg) are administered per dose in mice. Typically, the doses of AAV vectors to be administered in humans may range from $10^9$ to $10^{12}$ vg, preferably per eye.

The vector of the invention can thus be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient (i.e. the vector of the invention). The precise nature of the carrier or other material may be determined by the skilled person according to the route of administration, i.e. here subretinal injection. The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. For injection, the active ingredient will be in the form of an aqueous solution, which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives such as detergents to avoid binding to injection materials (i.e. Pluronic) may be included, as required. For delayed release, the vector may be included in a pharmaceutical composition, which is formulated for slow release, such as in microcapsules formed from biocompatible polymers or in liposomal carrier systems according to methods known in the art. Typically, the pharmaceutical composition of the present invention is supplied in a prefilled syringe. A "ready-to-use syringe" or "prefilled syringe" is a syringe which is supplied in a filled state, i.e. the pharmaceutical composition to be administered is already present in the syringe and ready for administration. Prefilled syringes have many benefits compared to separately provided syringe and vial, such as improved convenience, affordability, accuracy, sterility, and safety. The use of prefilled syringes results in greater dose precision, in a reduction of the potential for needle sticks injuries that can occur while drawing medication from vials, in pre-measured dosage reducing dosing errors due to the need to reconstituting and/or drawing medication into a syringe, and in less overfilling of the syringe helping to reduce costs by minimising drug waste. In some embodiments the pH of the liquid pharmaceutical composition of the present invention is in the range of 5.0 to 7.0, 5.1 to 6.9, 5.2 to 6.8, 5.3 to 6.7 or 5.4 to 6.6.

Notwithstanding the claims, the present invention is also defined by way of the following clauses.

Clause 1. A method of expressing a polynucleotide of interest in the cone photoreceptors of a subject comprising the subretinal delivery of a therapeutically effective amount of a recombinant AAV9-derived vector comprising a VP1 capsid protein as set forth in SEQ ID NO: 11 and the polynucleotide of interest under the control of the pR1.7 promoter as set forth in SEQ ID NO: 12.

Clause 2. The method of clause 1 wherein the subject is affected or likely to be affected with a retinal disease affecting cone photoreceptors.

Clause 3. The method of clause 1 wherein the subject suffers from a retinal disease selected from the group consisting of age-related macular degeneration, Bassen-kornzweig syndrome, choroideremia, gyrate atrophy, Refsum syndrome, Usher syndrome, color blindness, blue cone monochromacy, achromatopsia, incomplete achromatopsia, oligocone trichromacy, retinitis pigmentosa (RP), macular degeneration, Stargardt's Disease, Bardet-Biedl syndrome, Bornholm eye disease, Best's Disease and Leber's congenital amaurosis.

Clause 4. The method of clause 1 wherein the polynucleotide of interest encodes for retinitis pigmentosa GTPase regulator (RPGRORF15), CNGB3 (beta subunit of the cone cyclic nucleotide-gated cation channel), CNGA3 (alpha subunit of the cone cyclic nucleotide-gated cation channel) or GNAT2.

Clause 5. The method of clause 1 wherein the polynucleotide of interest encodes for a neurotrophic factor.

Clause 6. The method of clause 1 wherein the polynucleotide of interest encodes forRdCVF, RdCVF2, RdCVFL or RdCVFL2.

Clause 7. The method of clause 1 wherein the polynucleotide of interest encodes for an opsin such as rhodopsin like halorhodopsin or cruxhalorhodopsin, photopsin, L/M wavelength (red/green) cone-opsin, or short wavelength (S) cone-opsin (blue).

Clause 8. The method of clause 7 wherein the polynucleotide of interest encodes for an opsin consisting of an amino acid sequence as set forth in SEQ ID NO: 13, SEQ ID NO: 14 or SEQ ID NO: 15.

Clause 9. The method of clause 1 wherein the polynucleotide of interest encodes for a site-specific endonuclease that provides for site-specific knock-down of gene function selected from the group consisting of zinc finger nucleases (ZFNs); transcription activator-like effector nucleases (TALENs), and CRISPR-associated endonucleases.

Clause 10. The method of clause 1 wherein the polynucleotide of interest encodes for Cas9 nuclease.

Clause 11. The method of clause 1 wherein the polynucleotide of interest encodes for an interfering RNA (RNAi), in particular a siRNA or shRNA.

Clause 12. The method of clause 1 wherein the polynucleotide of interest encodes for an antisense oligonucleotide.

Clause 13. The method of clause 1 wherein the subretinal delivery is performed at distance of the fovea without detaching said region.

Clause 14. A recombinant AAV9-derived vector comprising a VP1 capsid protein as set forth in SEQ ID NO: 11 and a polynucleotide of interest under the control of the pR1.7 promoter as set forth in SEQ ID NO: 12.

Clause 15. The recombinant AAV9-derived vector of clause 14 for use in a method for the treatment of a retinal disease affecting cone photoreceptors.

The invention will be further illustrated by the following figures and examples. However, these examples and figures should not be interpreted in any way as limiting the scope of the present invention.

EXAMPLE

Figure 1:
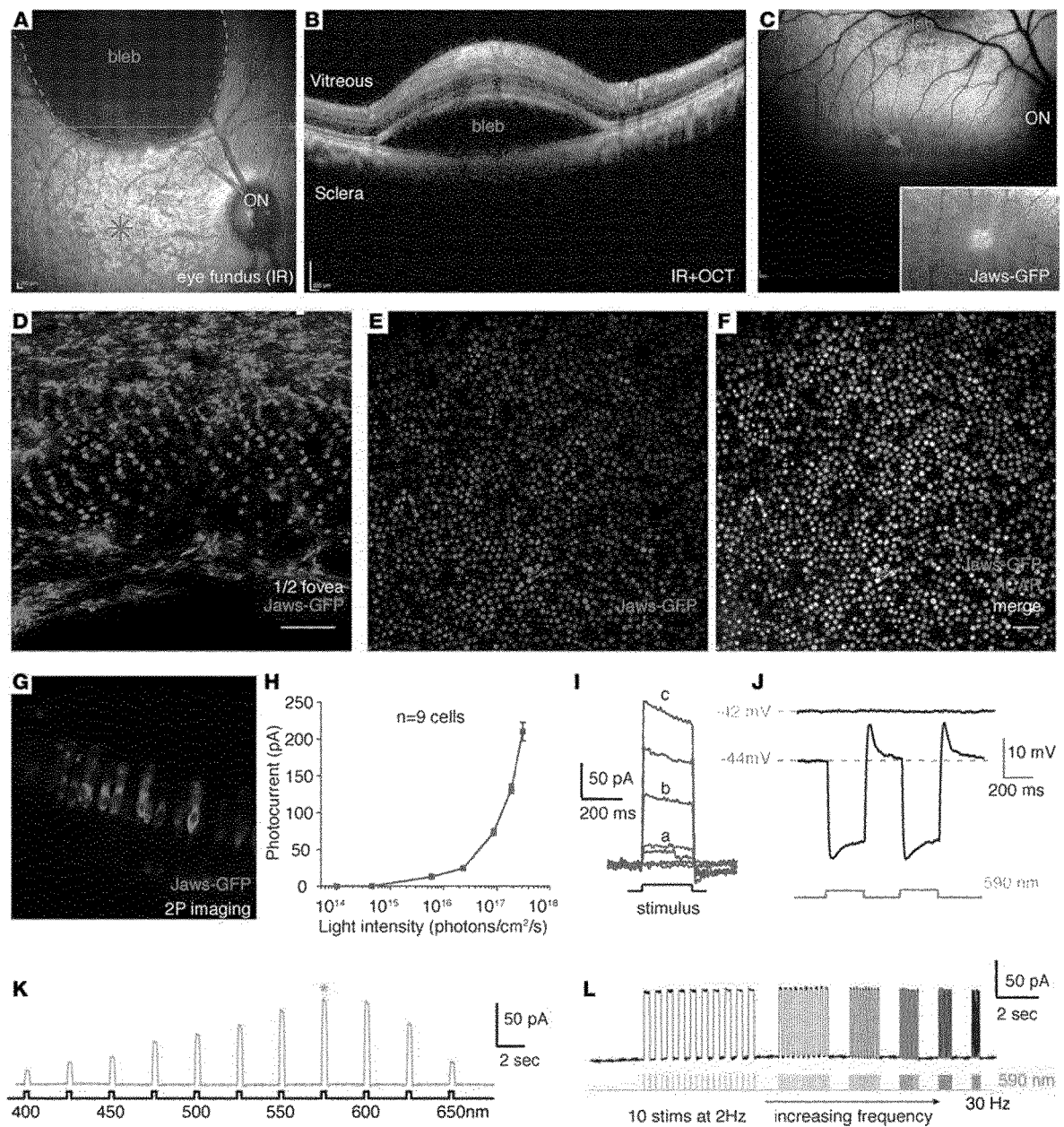
FIG. 1. AAV9-7m8 transduces the fovea via delivery in a distal bleb and provides robust optogenetic light responses with PR1.7-Jaws. (A) Eye fundus infrared image and (B) optical coherence tomography (OCT) image immediately after subretinal delivery of AAV9-7m8 in peripheral retina. (C) Eye fundus fluorescence image 1 month after injection shows strong Jaws-GFP expression within the subretinal bleb and away from the injection site, including the fovea. Inset magnification: ×1.5. (D-F) Foveal flatmount shows highly efficient and specific foveal transduction using subretinal AAV9-7m8-PR1.7-Jaws-GFP. Scale bar: 50 μm. (G-L) Characteristics of the light responses triggered by optogenetic stimulation of Jaws. (G) Lateral view of Jaws-expressing cones in living tissue using 2-photon imaging. (H and I) Whole-cell patch clamp recordings of Jaws-GFP+ macaque cones. Jaws-induced photocurrents as a function of light intensity. Stimuli were applied from $1 \times 10^{14}$ to $3 \times 10^{17}$ photons cm-2 s-1 (n=9 cells from 2 retinas of 2 animals). (J) Jaws-GFP+ cones recorded in current-clamp configuration in current zero mode (with resting membrane potential indicated in gray), displaying light-elicited hyperpolarizations followed by short depolarizations. (K) Jaws-induced photocurrents as a function of stimulation wavelength in subretinally injected macaque eye. Stimuli were applied from 400-650 nm, separated by 25-nm steps, at an intensity equal to $8 \times 10^{16}$ photons cm-2·s-1. Maximal responses were obtained at 575 nm (asterisk). (L) Characterization of temporal properties. Modulation of Jaws-induced membrane photocurrents at increasing stimulation frequencies in Jaws-expressing macaque cones, from 2-30 Hz, at $8 \times 10^{16}$ photons cm-2·s-1. AAV, adeno-associated virus; PR1.7: promoter of 1.7 kilobases in length, based on the human red opsin gene enhancer and promoter sequences; IR: infrared.

Material & Methods:

AAV Production

AAV vectors were produced as previously described using the co-transfection method and purified by iodixanol gradient ultracentrifugation (49). AAV vector stocks were titered by quantitative PCR (50) using SYBR Green (Thermo Fischer Scientific).

Animals and Intraocular Injections

Wild-type C57BL6/j (Janvier Labs) or rd10 mice (bred and raised in the animal facility of the Vision Institute), and cynomolgus macaques (Noveprim, Mauritius) were used for this study.

For eye injections (n=6 eyes/condition), 6-week old female mice were anesthetized by isofluorane inhalation. Pupils were dilated and a 33-gauge needle was inserted into the eye to deliver 2 μL of AAV vector solution intravitreally or 1 μL subretinally.

Regarding macaque eye injections, macaques were first selected based on absence of neutralizing antibody titers against AAV. Prior to surgery, primates were anesthetized with an intramuscular injection of 10 mg/kg ketamin and 0.5 mh/kgxylazine. Anesthesia was maintained with an intravenous injection of propofol, 1 ml/kg/h (PropoVet Multidose 10 mg/ml, Zoetis). Then, their pupils were dilated and their eyelids were kept open using eyelid speculum. A 1-ml syringe equipped with a 32-mm, 27-gauge needle was used for intravitreal injections. The needle was inserted into the sclera approximately 2 mm posterior to the limbus to deliver 100 μl of the viral vector solution. Finally, the needle was slowly removed. Animals did not receive local corticosteroid injections.

For subretinal AAV injections, two 25-gauge vitrectomy ports were set approximately 2 mm posterior to the limbus, one for the endo-illumination probe and the other for the subretinal cannula. A 1-ml Hamilton syringe equipped with a 25-gauge subretinal cannula with a 41-gauge tip was used for the injection. The endoillumination probe and cannula were introduced into the eye. The viral vector solution (50 μl) was injected subretinally to create a bleb either below or above the fovea. The instruments were then withdrawn. Eyes received corticosteroid treatment (47) that consisted of a laterobulbar injection of 12 mg of Kenacort (Bristol-Myers Squibb) except right eye of NHPS. After subretinal or intravitreal vector administration, opthtalmic steroid and antibiotic ointments (Fradexam, TVM) were applied to the corneas after injections.

In Vivo Macaque Eye Imaging

After pupil dilation, a Spectralis HRA+OCT system (Heidelberg Engineering, Germany) was used to acquire OCT images, and fluorescent images of GFP using the "Fundus Autofluoresence mode" which consists of and excitation wavelength of 488 nm and barrier filter of 500 nm.

Two-Photon Imaging and Ex-Vivo Electrophysiological Recordings of Macaque Retinas A two-photon microscope equipped with a 40× water immersion objective (LUMPLFLN40x/W/0.80, Olympus) with a pulsed femto-second laser (InSight™ DeepSee™—Newport Corporation) was used for imaging GFP-positive retinal cells from whole-mount retinas (with photoreceptor-cell-side up) or retina slices (vertical sections). AAV-treated macaque retinas were isolated and later imaged in oxygenized (95% 02, 5% CO2) Ames medium (Sigma-Aldrich). For live two-photon imaging, retinas were placed in the recording chamber of the microscope, and z-stacks were acquired using the excitation laser at a wavelength of 930 nm. Images were processed offline using ImageJ (NIH). For whole-cell patch-clamp recordings, an Axon Multiclamp 700B amplifier was used. Electrodes were made from borosilicate glass (BF100-50-10, Sutter Instruments) and pulled to 6-9 MΩ. Pipettes were filled with 115 mM K Gluconate, 10 mM KCl, 1 mM MgCl2, 0.5 mM CaCl2, 1.5 mM EGTA, 10 mM HEPES, and 4 mM ATP-Na2 (pH 7.2). Cells were clamped at a potential of −40 mV in voltage-clamp configuration, or recorded in current-clamp (current zero) configuration. Retinas were dark-adapted at least half an hour in the recording chamber prior to recordings.

Human iPSC Cultures

We have generated retinal organoids from human iPSCs based on a previously published protocol (37). Clone hiPSC-2 was expanded and differentiated on fibroblast feeders from postnatal human foreskins (ATCC CRL 2429) in "proneural medium" as already described (37). Starting from highly confluent adherent iPS cell cultures and in the absence of fibroblast growth factor 2 (FGF2), self-forming retinal organoids can be identified after 2 weeks. At this point, the organoids were mechanically isolated and cultured in 3D conditions for up to 43 days. FGF2 was supplemented to the medium in 3 conditions for 7 days after the mechanical isolation of the organoids to promote their growth. The retinal organoids were infected at day 28 of differentiation at a dose of $5\times10^{10}$ vg/organoid with AAV2-7m8 vectors carrying the GFP gene under the control of pR1.7 promoter. 10 μM DAPT (Selleck) was added to the medium for a week from day 28 on to promote cell cycle arrest of the existent cell populations. Fluorescence intensity was observed for the first time 5 days after infection and continued to increase up to day 43.

Human Post-Mortem Retinal Explants

Human retinal explants were prepared using a previously described protocol (38). Briefly, eyes were dissected in CO2-independent-medium (Thermo Fischer Scientific). The anterior parts were removed, retina was isolated and cut into small pieces. These explants were placed photoreceptor side-up on a Transwell cell culture insert (Corning), and 2 mL of Neurobasal medium (Thermo Fischer Scientific) supplemented with B27 (Thermo Fischer Scientific) were added to each well below each explant. The following day, each explant was infected with a single 0.5 μL drop of AAV-pR1.7-GFP containing $10^{10}$ viral particles. Vector-infected explants were incubated for 10-15 days to allow GFP expression, which was checked using an epifluorescence macroscope.

Histology, Immunohistochemistry and Microscopy

Mouse eyes were enucleated and immediately fixed in 10% formalin-4% formaldehyde for 2 hours for cryosections. Macaque retinas were fixed after dissection in 4% formaldehyde for 3 hours. Retinal organoids and human retinal explants were rinsed in PBS at the end of their culture periods and fixed in 4% paraformaldehyde for 10 minutes. For cryosections, mouse and macaque retinas, retinal organoids and human retinal explants were immersed in PBS-30% sucrose overnight at 4° C. Mouse eyecups, human retinal explants, macaque retinas were embedded in OCT (optimal cutting temperature) medium and frozen in liquid nitrogen, while retinal organoids were embedded in 7.5% gelatin and 10% sucrose in PBS and frozen in dry ice-cold isopentane. 10 µm-thick vertical sections were cut with a Microm cryostat. After incubation in the blocking buffer, sections were incubated with primary antibodies overnight at 4° C.: human Cone Arrestin (hCAR) antibody (gift from Cheryl Craft, University of Southern California, Los Angeles, USA); M/L opsin antibody (Millipore AB5405), and mouse Cone Arrestin antibody (Millipore, AB15282). After multiple washes of the sections, the secondary antibodies (Alexa Fluor 488, 594 or 647, ThermoFisher) and DAPI were added, followed by several washes. Retinal flatmounts or cryosections were mounted in Vectashield mounting medium (Vector Laboratories) for fluorescence microscopy, and retinal sections were visualized using an Olympus Upright confocal microscope and then analyzed with Fiji Software. Three-dimensional projections of the fovea were created with Imaris software (Bitplane).

In Silico Identification of Potential Regulatory Elements and Transcriptomic Analysis TF binding site analysis was performed on red opsin gene promoter sequence —pR2.1 and pR1.7 sequences- and the cone arrestin 3 genomic region. The TRANSFAC database 8.3 (a1ggen.1si.upc.es/) was used for TF binding site prediction. Each TF from the predicted list was analyzed using the Knowledge Base for Sensory System (KBASS, kbass.institut-vision.org/KBaSS/transcriptomics/index.php) to select those expressed in human retina using the transcriptomic experiment RNG209 (51). A filter was used to retain TFs with a signal intensity value superior to 40 units in the sample prepared from the experiment RNG209 after normalization by Robust Multi-array Average (RMA) as previously described (52). In this experiment, human retinal specimens used as controls were post-mortem specimens collected within 12 hours following death of patients with no past medical history of eye disease or diabetes. Nineteen samples were collected from 19 eyes representing 17 patients. Sex ratio was 12 men/7 women with a mean age of 61 years (range 25-78 years).

Statistics

Data were analyzed using a one-way Anova test in Graphpad Prism (multiple comparison, Tukey correction). Error bars on the graphs show the Standard Error of the Mean (SEM). p values are expressed as the following *p<0.033, ns: non-significant.

Study Approval

For animals, the experiments were realized in accordance with the National Institutes of Health Guide for Care and Use of Laboratory Animals. The protocols were approved by the Local Animal Ethics Committees and conducted in accordance with Directive 2010/63/EU of the European Parliament. Postmortem human ocular globes from donors were acquired from the School of Surgery (Ecole de Chirugie, Assitance Publique Hôpitaux de Paris). The protocol was approved by the institutional review boards of the School of Surgery and the Quinze-Vingts National Ophthalmology Hospital. All experiments on postmortem human retinal explants were performed according to the local regulations as well as the guidelines of the Declaration of Helsinki.

Results:

Selection of a Strong and Specific Cone-Cell Specific Promoter in Murine Models

In order to find vector-promoter combinations suitable for strong and specific cone targeting away from the injection site, we compared several AAVs after intravitreal and subretinal delivery in mouse retinas. To enable efficient cone photoreceptor targeting, we used an engineered AAV variant called AAV2-7m8, which has been shown to target photoreceptors efficiently via both administration routes (16, 17). Specific targeting of cone cells has never been attempted using vitreally administered AAV. In order to find suitable promoter sequences for restricted gene expression in cones applicable in the clinic, we focused on promoters that have previously been validated in either non-human primate (NHP) (18) or human tissue (4). We generated AAV2-7m8 vectors encoding GFP under the control of mCAR (mouse Cone Arrestin), pR2.1 and pR1.7 promoters (synthetic promoters based on the human red opsin gene enhancer and promoter sequences) and injected them at equal titers into eyes of six weeks old wild-type mice. Three weeks after subretinal injections, retinal cross-sections were stained with cone arrestin and GFP expression was examined (data not shown). We found high GFP expression in both rod and cone photoreceptors with mCAR promoter while pR2.1 and pR1.7 lead to strong expression mostly in cones. Using the same vectors, we obtained strikingly different expression patterns after intravitreal delivery (data not shown). mCAR promoter lead to GFP expression in some cones, but was leaky towards rods as well as cells of the inner nuclear layer (INL) and ganglion cell layer (GCL) (data not shown). Both pR2.1 and pR1.7 promoters lead to more cone labeling than mCAR promoter (data not shown). pR2.1 transduced more cones than pR1.7 but, it also produced non-specific GFP expression in the INL and GCL. Only the pR1.7 promoter showed GFP expression in cones with minimal expression in rods and was not leaky towards the inner retina (data not shown). Finally, as retinal disease state can influence AAV-mediated gene delivery and transgene expression patterns (20, 21) we validated AAV2-7m8-pR1.7 vector-promoter combination in a mouse model of retinal degeneration. We injected AAV2-7m8-pR1.7-GFP intravitreally in the rd10 mouse model of retinitis pigmentosa. Two months after injection, GFP expression was restricted to cones (data not shown) supporting the suitability of this vector for cone-directed gene therapy via both intravitreal and subretinal injections.

Bioinformatic Analysis of mCAR, pR1.7 and pR2.1 Promoter Sequences Before moving onto further studies in other species, we aimed to better understand the reasons behind the divergent expression patterns obtained with the three promoters. To do so, we analyzed transcription factor (TF) binding sites within each promoter sequence using bioinformatics (data not shown). The present analysis aimed to answer the following questions: (i) why is pR1.7 more efficient than pR2.1 in cones? (ii) why do pR2.1 and mCAR promoters lead to off-target expression after intravitreal administration? We hypothesized that the differential expression patterns observed between pR1.7 and pR2.1 are due to additional TF binding sites found in the 337 bp sequence located in the 5' region of pR2.1 promoter but not in pR1.7 promoter (data not shown). Interestingly, we found a chicken ovalbumin upstream promoter-transcription factor I (COUP-TFI) binding site within this 337 bp sequence (data not shown). COUP-TFI has been shown to suppress green opsin gene (Opn1mw) expression in the mouse retina (22) and might thus be accountable for lower expression with pR2.1 promoter in macaque cones when AAV is delivered subretinally. Within the same specific 337 bp region, we also found multiple binding sites for generic, ubiquitous activator TFs (data not shown), such as CCAAT/enhancer binding protein beta (CEBPB) and general transcription factor II-I (GTF2I). These additional binding sites of TFs that enhance binding and basal transcriptional machinery assembly and that are not specifically expressed in cones might be responsible for some of the off-target expression observed with pR2.1 compared to pR1.7 (data not shown). We also analyzed TF binding sites in the genomic mCAR promoter sequence (also known as mouse Arr3) to explain the lack of specificity using the short version of this promoter used in the AAV constructs. The short sequence consists of a 521 bp portion of the genomic proximal CAR promoter (data not shown) presenting a TATA-box, a TATA-like box, as well as binding sites for CRX (Cone-rod homeobox protein) and SP (Specificity Protein) TFs (23) (data not shown). However, the 'Reg' sequence modulating CAR promoter activity (23) located directly upstream of the 521 bp region is excluded from the short mCAR sequence (data not shown). Based on the interactome of the TFs binding mCAR promoter obtained from the STRING database (24), CRX and SP TFs interact with each other and with RARA (Retinoic Acid Receptor Alpha), RXRA (RetinoidxReceptor Alpha) and THRB (Thyroid Hormone Receptor Beta) TFs (data not shown). These three nuclear receptors (NR) are involved in cell-type specific regulation of gene expression via MED1 (25) (Mediator Complex Subunit 1) by forming a cell-specific transcription co-activator complex (26, 27) (data not shown). CRX and SP binding sites are located on the 521 bp region, while RXRA, RARA and THRB binding sites are positioned on the Reg region (data not shown). Moreover, the Reg region contains five binding sites for THRβ2, an important nuclear receptor expressed in cones (28) (data not shown). For all of these reasons, removal of the Reg region is likely responsible for the off-target expression observed with the short mCAR promoter.

Safe Gene Delivery to Macaque Foveal Cones Via Intravitreal Administration of AAV Others and we have shown transduction of macaque cones using AAV variants with ubiquitous promoters (16, 29-31), but achieving cone transduction by vitreally administered AAV has only been possible at high doses leading to inflammation (16, 29). We reasoned that foveal cone targeting could be achieved if we use a strong cone-specific promoter at lower intravitreally injected AAV doses compatible with safety (29, 32). To test if such "dose sparing" is possible, we injected two macaque eyes with AAV2-7m8-pR1.7-GFP and 2 other macaque eyes with AAV2-7m8-CMV-GFP at a dose of $10^{11}$ viral genome (vg) (Table 1). Using in vivo eye fundus imaging, we observed GFP expression as early as two weeks post-injection with CMV and increased until 2 months after injection (data not shown). GFP fluorescence was predominantly in the periphery and in the parafoveal region. GFP expression with pR1.7 became detectable 6 to 8 weeks after administration and was restricted to the fovea (data not shown). There was no detectable damage to the fovea as assessed by Optical Coherence Tomography (OCT) (data not shown). Animals were sacrificed at 3 months post-injection. We then prepared flatmounts of the maculas (data not shown) and retinal cryosections at the level of the fovea (data not shown) and imaged GFP fluorescence using confocal microscopy, with equal acquisition settings for each eye. These images corroborated the in vivo findings and show specific and robust cone transduction from the vitreous, at a dose of $10^{11}$ particles, using AAV2-7m8-pR1.7. About 58% of the hCAR$^+$ cells were found to express detectable levels of GFP in the foveola. Using a similar dose, it is not possible to transduce cones with CMV (no detectable transgene expression).

TABLE 1

Summary of injections in nonhuman primates

| Animal | Age (years) | Weight (kg) | Sex | Injection type; eye | AAV capsid | Transgene | Dose (vg/eye) | Volume (µl) |
|---|---|---|---|---|---|---|---|---|
| NHP1 | 7 | 8.65 | M | intravitreal; LE | AAV2-7m8 | PR1.7-GFP | $1 \times 10^{11}$ vg | 100 |
| NHP2 | 8 | 11.81 | M | intravitreal; LE | AAV2-7m8 | CMV-GFP | $1 \times 10^{11}$ vg | 100 |
| NHP3 | 13 | 12.93 | M | intravitreal; LE | AAV2-7m8 | PR1.7-GFP | $1 \times 10^{11}$ vg | 100 |
|  |  |  |  | intravitreal; RE | AAV2-7m8 | CMV-GFP | $1 \times 10^{11}$ vg |  |
| NHP4 | 4 | 5.03 | M | intravitreal; RE | AAV2-7m8 | PRL7-Jaws-GFP | $1 \times 10^{11}$ vg | 100 |
| NHP5 | 4 | 6.26 | M | subretinal, sup; RE | AAV9-7m8 | PRL7-Jaws-GFP | $1 \times 10^{10}$ vg | 50 |
|  |  |  |  | intravitreal; LE | AAV2-7m8 | PRL7-Jaws-GFP | $1 \times 10^{10}$ vg | 50 |
| NHP6 | 5 | 6.83 | M | subretinal, sup; RE | AAV9-7m8 | PRL7-Jaws-GFP | $5 \times 10^{10}$ vg | 50 |
| NHP7 | 3 | 3 | M | subretinal, inf; RE | AAV9-7m8 | PRL7-Jaws-GFP | $5 \times 10^{9}$ vg | 50 |
| NHP8 | 3 | 3.23 | M | subretinal, inf; RE | AAV9-7m8 | PRL7-Jaws-GFP | $5 \times 10^{9}$ vg | 50 |

NHP, nonhuman primate; kg, kilograms; M, male; sup, superior bleb; inf, inferior bleb, LE, left eye; RE, right eye; AAV, adeno-associated virus; CMV, cytomegalovirus promoter; PR1.7, Promoter 1.7 kilobases, based on human red opsin gene enhancer and promoter sequences; vg, viral genome.

Therapeutic Gene Delivery to Foveal Cones for Vision Restoration Using Optogenetics We next aimed to evaluate the possibility of using this promoter for therapeutic gene delivery. There is no existing blind macaque or primate model of retinal degeneration to test functional outcomes after gene replacement (i.e. CNGB3 for treatment of achromatopsia). However, it is possible to evaluate vision restoration in wild-type macaques using optogenetic strategies since we can distinguish between optogenetic-mediated light responses versus endogenous cone opsin-mediated responses (4). We evaluated the potential of optogenetic vision restoration by expression of Jaws, a hyperpolarizing microbial opsin (15), in foveal cones. We injected one macaque with $10^{11}$ vg of AAV2-7m8-pR1.7-Jaws-GFP in the vitreous to evaluate its therapeutic potential for reactivation of dormant cones in mid-stage retinitis pigmentosa as described previously in mice (4,15). We found high-level Jaws-GFP expression restricted to the foveal cones in the injected eyes (data not shown) similar to GFP expression alone (data not shown). The animal was then sacrificed two months post injection and half of the retina was processed for histology. Retinal flat-mounts showed typical anatomy of cones in the foveola, the region of the fovea that contains densely packed cones responsible our high acuity vision. Immunostaining for cone arrestin was used to quantify transduced cones (data not shown). About 50 percent of the cone arrestin positive cells (hCAR$^+$) were found to express detectable levels of Jaws-GFP in this retina. The other half of the retina was conserved as explants (33) for characterization of optogenetic light responses arising from the hyperpolarizing pump Jaws (data not shown). Electrophysiological recordings were performed on transduced cones expressing Jaws and in control cones without GFP expression (data not shown). Whole-cell patch-clamp recordings in GFP positive Jaws-cones exhibited robust light responses to orange light flashes (n=4) (data not shown). Action spectrum of recorded cells showed that highest light responses were obtained using orange light between 575 and 600 nm (data not shown) as previously shown for Jaws (14). Jaws-expressing cones recorded in current-clamp configuration displayed light-elicited hyperpolarizations followed by short depolarizations (n=4 cells), while control cones did not respond to the same light stimuli (n=3 cells) (data not shown).

Finally, we injected intravitreally another macaque eye with $10^{10}$ particles of AAV2-7m8-pR1.7-Jaws-GFP to evaluate feasibility of foveal transduction at even lower doses. We obtained detectable foveal Jaws expression even with this lower dose, although expression levels were lower than with $10^{11}$ particles (data not shown). Altogether, all 4 macaque eyes injected with AAV2-7m8-pR1.7-GFP (n=2) or Jaws-GFP (n=2) show reproducibility and strength of intravitreal approach compatible with optogenetic reactivation of cones.

Figure 2:
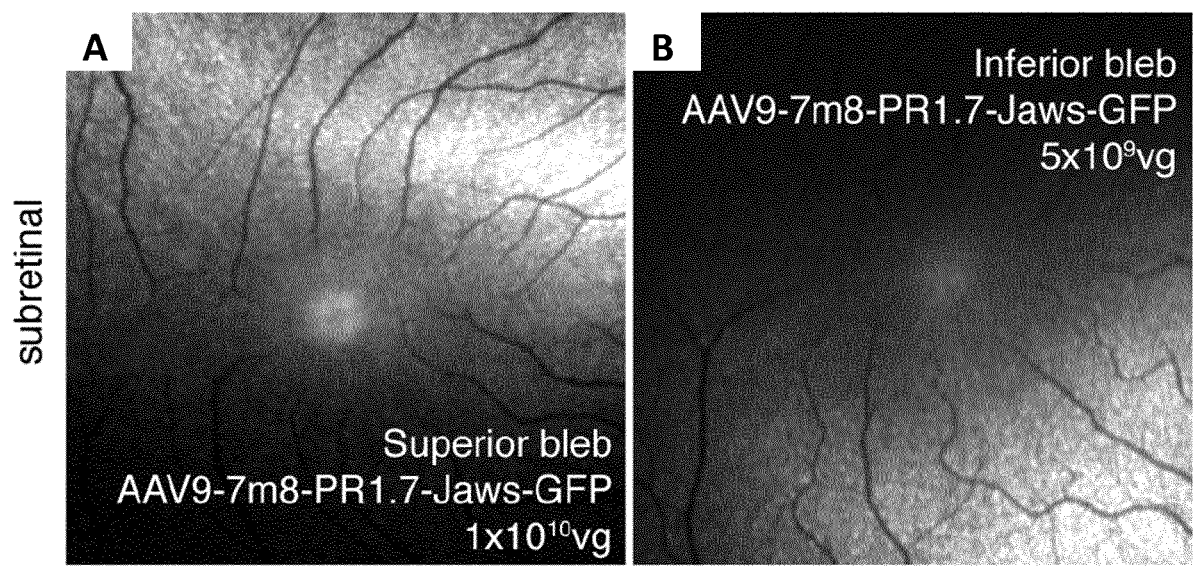
FIG. 2. Macaque eye fundus images for characterization of dose response. Jaws-GFP expression two weeks after subretinal injection of $1 \times 10^{10}$ particles (n=1 eye, superior bleb) (A) and $5 \times 10^{9}$ particles (n=2 eyes, inferior blebs) (B) of AAV9-7m8-PR1.7-Jaws-GFP.
Figure 3:
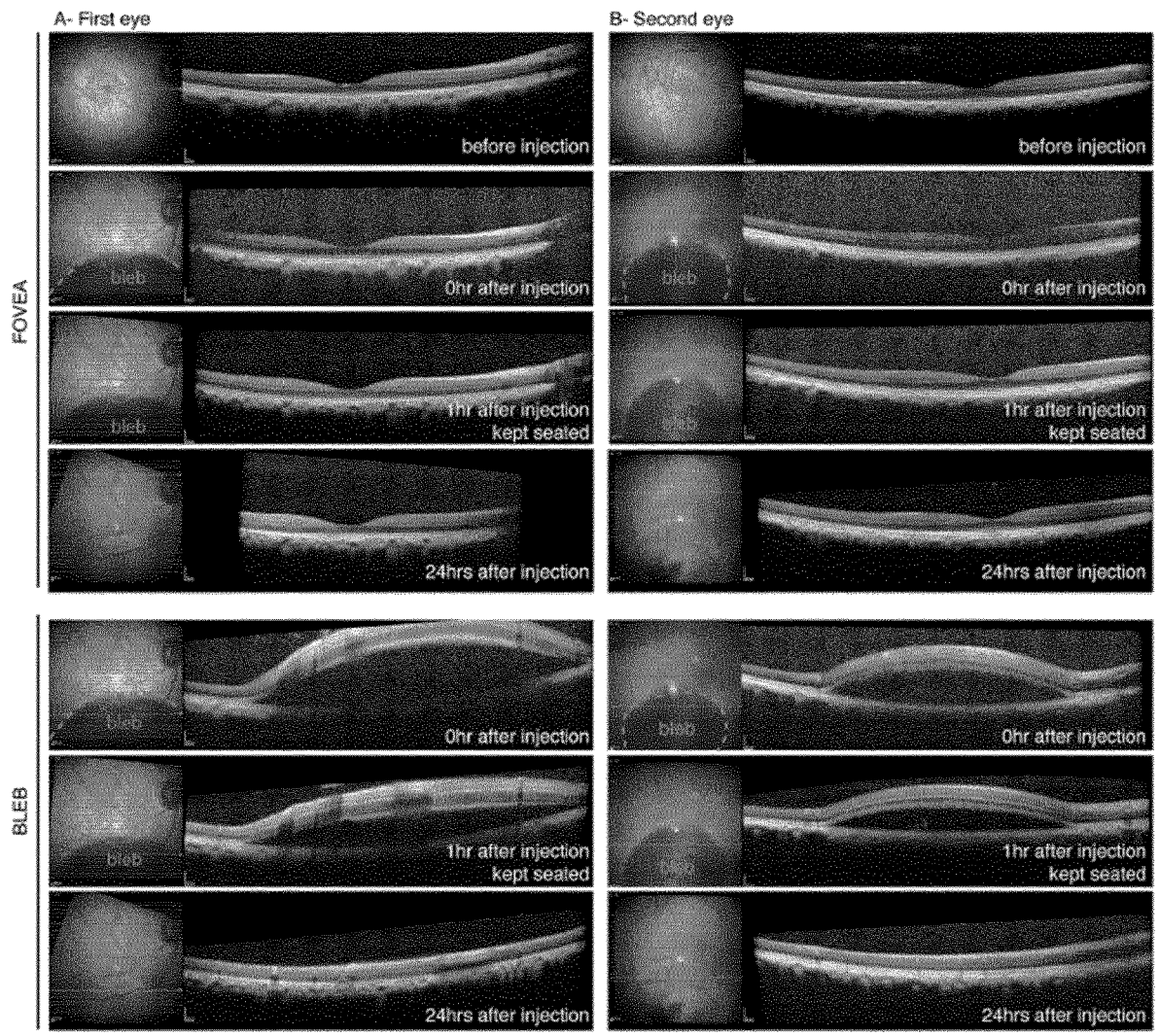
FIG. 3. Distal inferior subretinal administration follow-up using in vivo eye fundus and optical coherence tomography (OCT) imaging. Images were acquired before and after peripheral injection of AAV9-7m8-PR1.7-Jaws-GFP, $5 \times 10^{9}$ viral particles (n=2 eyes). Eye fundus infrared image is centered on the macula and OCT image was taken at the level of the fovea or at the level of the bleb shortly before and after the injections. Follow-up images were acquired one hour after injections while the animal was kept seated. Another image was acquired 24 hours after injections. Bleb: subretinally injected fluid; hrs: hours; Asterisk: fovea; bold arrow: OCT image of the retina highlighted, shown on the right part of each image; dashed line: delimitation of the bleb.

Enhanced Optogenetic Responses in Foveal Cones Via Distal Subretinal Administration of AAV9-7m8-Jaws Transduction of foveal cones via intravitreal injection of AAV2-7m8 with a strong cone promoter is likely an ideal approach to treat cones in fragile retinas of retinitis pigmentosa patients with dormant cones present mainly in the foveola. However, for achromatopsia patients, as well as the subset of retinitis pigmentosa patients with strong neutralizing antibody titers against AAV2 (32), a subretinal approach might be advantageous. Previous studies have shown that subretinal injection of AAV9 leads to efficient transgene expression in cones both centrally and peripherally at low doses, likely due to the abundance of galactosylated glycans, the primary receptor for AAV9, on cone photoreceptors (30, 34). Based on this, we reasoned that an enhanced AAV9 variant might afford efficient transduction of foveal cones from a distal bleb. To promote foveal cone gene delivery through a distal subretinal injection site, we used AAV9-7m8 variant which provides a 30-fold increase in infectivity over wild type AAV9. We injected one animal subretinally with $5 \times 10^{10}$ particles of this vector encoding Jaws-GFP into the peripheral retina (FIG. 1, A-B) without detaching the fovea. As early as two weeks post-injection we observed strong Jaws-GFP fluorescence in the bleb (delimited by the dashed line), and also in the foveola (FIG. 1C). Fluorescence intensity was higher in the foveola compared to intravitreally-treated retinas. We observed the same data with a second eye injected with a lower dose of $10^{10}$ vg of the same vector (FIG. 2A). To further confirm that the superior peripheral blebs did not descend toward the fovea once the animal was in upright position and to see if further dose reduction was possible, we injected 2 other eyes with a dose of $5^{10}$ vg, this time inferior to the fovea (Table 1). Using OCT, we observed that the fovea was not detached after surgery (FIG. 3). The same expression pattern, extending to the foveal cones, was obtained in these retinas (FIG. 2B). These results collectively show the reproducibility of this approach and its compatibility with low viral doses.

Retinal flatmounts were then prepared. Fovea was processed for histology and showed strong Jaws-GFP expression in a large population of cones (FIG. 1D) in the region between the injection site and inside the fovea (FIG. 1, D-F). Cell counting of GFP and cone-arrestin positive (CAR$^+$) cells in the fovea showed about 95 percent of cones were labeled using this subretinal approach (FIG. 1, E-F) compared to about 50 percent obtained with intravitreal injection (data not shown). The amplitude of photocurrents were 5 times higher in Jaws cones after subretinal delivery (FIG. 1, G-H) compared to those in Jaws cones after intravitreal delivery (data not shown), with similar shape light sensitivity curves. This is likely due to higher Jaws expression in cones transduced subretinally compared to cones transduced intravitreally. Temporal analysis using flicker stimulation at different frequencies showed very fast and robust photocurrent responses from 2 Hz up to 30 Hz at $8 \times 10^{16}$ photons cm$^{-2}$ s$^{-1}$ (FIG. 1L). In both cases the light intensity response threshold was observed at around $10^{15}$ photons cm$^{-2}$ s$^{-1}$. While recording cones in current-clamp configuration in current zero mode, enables the experimenter to record the actual resting membrane potential of the cells, we observed light-elicited hyperpolarisation (FIG. 1, I-J), followed by short depolarization that were more visible with subretinally injected retinas, correlating with higher expression levels of Jaws-GFP than in intravitreally injected retinas. Jaws-induced photocurrents varied in amplitude as a function of stimulation wavelength peaking at 575 nm, as expected (FIG. 1K). Application of increasing stimulation frequencies showed that reliable photocurrents could be obtained with return to baseline at up to 30 Hz, at $8 \cdot 10^{16}$ photons cm$^{-2}$ s$^{-1}$ (FIG. 1L).

pR1.7 Promoter Drives Strong and Highly Specific Gene Expression in Human Cones

Altogether our data in non-human primates show for the first time non-invasive, specific and high-level primate foveal cone transduction compatible with optogenetic applications for vision restoration. However as promoter activity shows important variations across species (29, 35, 36) we deemed it necessary to validate pR1.7 in human cells and tissues. Due to the lack of a good human photoreceptor cell line or other model that could be used to test efficiency of cone promoter activity, we used 3D retinal organoids derived from human induced Pluripotent Stem (iPS) cells (37). We generated photoreceptor-enriched retinal organoids and infected them with AAV2-7m8 vectors encoding GFP under the control of pR1.7 promoter (data not shown). GFP expression was observed as early as 5 days post infection and continued to increase until the experiment was terminated for analysis on day 43. GFP expression in these organoids colocalized with human Cone Arrestin (hCAR) immunostaining (data not shown). Lastly, as human retinal organoids do not represent all features of mature human retina, we validated the efficacy and specificity of pR1.7 promoter in post-mortem human retinal explants. Human retinal explants were cultured as described previously (38) and infected with a single drop of AAV2-7m8-pR1.7-GFP (data not shown). Fifteen days after infection, GFP expression was analyzed on cryosections. The expression was restricted to the ONL (data not shown) and co-localized with M/L-opsin, a cone cell marker (data not shown). These data collectively point towards high efficiency and specificity of pR1.7 in leading to restricted gene expression in human cones.

Eye-Injection In Vivo Safety Study

We then evaluated the immune response after intravitreal injections of AAV2-7m8-PR1.7-Jaws-GFP and subretinal injection of AAV9-7m8-PR1.7-Jaws-GFP.

Detection of Retinal Abnormalities and Infiltrates

Figure 4:
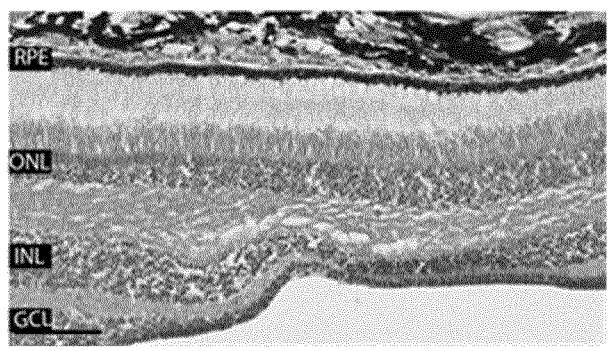
FIG. 4. Representative histological findings from animals injected with a high dose of AVV9-7m8-PR1.7-Jaws-GFP into the subretinal space. Scale bar 100 μm. RPE: retinal pigmented epithelium; ONL: outer nuclear layer; INL: inner nuclear layer; GCL: ganglion cell layer.

Inflammation (immune reaction) was evaluated 2 months after injection by H&E staining and inflammatory cell immunochemistry (IHC) on retinal cryosections. Based on H&E staining and microscopic observations in retinal sections, neither intravitreal administration of AAV2-7m8-PR1.7-Jaws-GFP (FIG. 4A) nor subretinal injections of AVV9-7m8-PR1.7-Jaws-GFP (FIG. 4B) were associated with cellular infiltrates or with retinal disorganization in contrast with Killer Red and GFP eyes in the previous part.

Immunohistochemistry for Detection of Inflammation Markers

Figure 5:
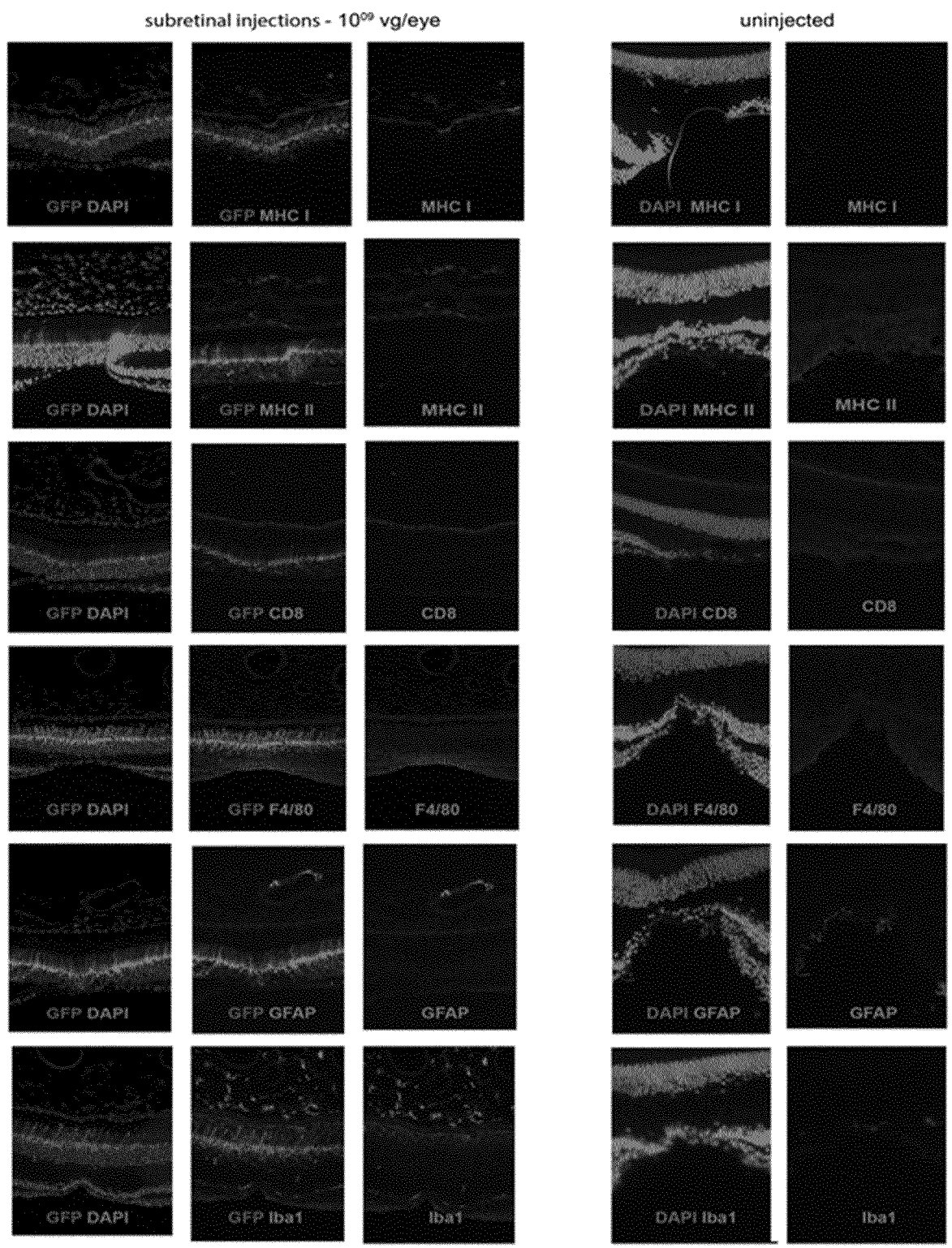
FIG. 5. Immunohistochemistry near the fovea suggests no adaptive cellular immune response after intravitreal injection. Left panels show a representative image from one of the 2 eyes treated with AAV9-7m8-PR1.7-Jaws-GFP (1010 vg) after subretinal injection. Right panels show a representative image of one of the 4 uninjected eyes.

To analyse the local adaptive immune response, we performed IHC analysis of monkey retinas injected with both AAV2-7m8-PR1.7-Jaws-GFP and AVV9-7m8-PR1.7-Jaws-GFP constructs. Cryosections from subretinally treated animals and intravitreally treated ones were stained with anti-Human HLA ABC (MHC I), anti-HLA-DR (major histocompatibility complex II (MHC II), anti-human CD8, anti-F4/80. None of the sections were positive for the above-mentioned markers. Staining for the glial fibrillary acidic protein (GFAP) ionized calcium-binding adaptor molecule 1 (IBA1), a hematopoietic marker for microglia and macrophages were negative (FIG. 5 related to AVV9-7m8-PR1.7-Jaws-GFP; data not shown for AAV2-7m8-PR1.7-Jaws-GFP).

Discussion:

The fovea accounts for less than 1% of the retinal surface area in primates yet it provides the input to about 50% of the cells in the primary visual cortex (1). The high concentration of cones in the fovea, the thinnest and most delicate part of the retina, allows for high acuity vision, and it is of utmost importance to preserve the unique functions (39) and architecture (40) of the cones in this area during therapeutic interventions. Foveal cones can be targeted via different administration routes, using either subretinal or intravitreal injections (35, 41, 42) but detaching the fovea might lead to mechanical damage, especially in the degenerating retina (43). For all of these reasons, ways to deliver therapeutics to the fovea, without detaching this region are needed. Intravitreal injections are a surgically simple way to deliver therapeutics without retinal detachment. Gene therapy vectors can target the outer retina via intravitreal injections in rodents without damage to the photoreceptors (17, 35). However, safe and efficient gene delivery to primate cones via intravitreal injection had not been achieved so far, likely due to the substantial dilution of the vector in the vitreous and resulting loss of efficacy. The use of cell-type specific promoters that provide high-level gene expression with a lower local concentration is critical to overcome this challenge (29, 44).

In this study, we sought to first achieve strong and exclusive transduction of cones via non-invasive, intravitreal injection using various promoters in combination with AAV2-7m8 capsid. We selected three promoters and tested them for specificity and strength of cone transduction side-by-side. All promoters tested in vivo in mouse retinas lead to transgene expression in the photoreceptor layer when delivered subretinally. The mCAR promoter led to expression in rods and cones. Surprisingly, after intravitreal delivery, only pR1.7 maintained its specificity towards cones, while pR2.1 and mCAR gave rise to non-specific gene expression in inner retinal neurons. mCAR and pR2.1 gave rise to non-specific expression in inner retinal cells, making them unsuitable for optogenetic applications where any expression in downstream neurons would cancel out the response from the photoreceptors. Subsequent in silico analysis of TF binding sites within each promoter sequence proposed basis for more specific transduction with pR1.7 and the observed the lack of specificity with the mCAR promoter. Next, to study the ability of AAV2-7m8 equipped with pR1.7 promoter to transduce foveal cones, we conducted gene delivery studies in macaque eyes. Complete restriction of gene expression to primate cones was achieved using AAV2-7m8-pR1.7 in the fovea via intravitreal administration.

One shortcoming with intravitreal injection route is the higher susceptibility of AAVs administered into this compartment to interactions with the immune system compared to subretinal administration (32). It has been shown that antibody neutralization poses a barrier to intravitreal AAV vector mediated gene delivery in non-human primates and this will likely pose a challenge for human application. We thus aimed to develop another gene delivery approach for patients who have neutralizing antibodies towards AAV2. To this aim we tested gene delivery to foveal cones by subretinal administration of AAV9-7m8 at a distal site (Table 2). We demonstrated that robust light responses could be obtained with this new delivery approach, thanks to the vector's ability to diffuse laterally and mediate expression outside of the bleb. Using the same optogenetic cone reactivation strategy, we showed that this approach also affords robust light responses mediated by Jaws but in a higher percentage of cones compared to intravitreal route (4, 15).

Our in vivo findings collectively point to three important considerations in retinal gene delivery. First, enhanced AAV vectors, whether obtained via directed evolution (AAV2-7m8 (35)) or rational design (AAV9-7m8 (17)), can achieve therapeutic objectives where parental serotypes fail to provide sufficient gene delivery. Indeed, AAV2 and AAV9 cannot perform efficient non-invasive foveal targeting (30, 31) while 7m8 modified vectors bridge this gap. Second, strong cell-type specific promoters allow dose sparing important for the safety of gene therapy (i.e. avoiding immune response). Third, our study shows the non-negligible impact of vector administration route on transgene expression patterns. Finally, to complement our in vivo results in animals, we performed a battery of ex vivo tests in human tissues that, in combination with in vivo experiments, constitute a versatile platform for validating gene therapy for clinical application. The vector-promoter combinations described here will find utility in all retinal diseases where cone targeting is desired. Each administration route and vector can be considered based on the serological state of the patient and natural history of the targeted disease (see Table 2). The combination of pR1.7 and AAV2-7m8 is ideal for therapeutic gene expression in human foveal cones when delivered into the vitreous and can be an ideal way to reanimate remaining dormant cones with optogenetics in retinitis pigmentosa (4). Since cones subsist in both the center and the periphery in achromatopsia, gene delivery in the periphery, using AAV9-7m8-pR1.7 can be more efficacious, as it would deliver the therapeutic gene into both the foveal and peripheral cones.

Our in vivo experiments further confirm the safety of the AAV9-7m8-pR1.7 and AAV2-7m8-pR1.7 vectors, since these did not elicit an immune response after injection.

TABLE 2

AAV vector administration strategies for cone-directed gene therapy

| Injection route | Peripheral SR | Central SR | Peripheral SR (near macula) | Intravitreal |
|---|---|---|---|---|
| Therapeutic gene expression | Peripheral | Central (macula-fovea) | Peripheral and central | Central |
| Potential capsids | AAV2-3YF(18, 47), AAV9 (18, 30, 47) | AAV2 in clinical trials (8, 9, 48) | AAV9-7m8 as used in this study | AAV2-7m8 as used in this study |
| Advantages | Immune privilege, High level therapeutic gene expression | Immune privilege, High level, therapeutic gene expression, Foveal transduction, High acuity vision | Immune privilege, High level therapeutic gene expression, Larger expression area, that includes the fovea High-acuity vision, Not invasive to the fovea | Noninvasive, Potential high acuity, vision, Controlled area of expression pattern |
| Disadvantages | Invasive, No foveal transduction, Low acuity vision | Invasive, risk of adverse effects such as macular thinning(11) |  | Presence of NAbs in the vitreous (use of glucocorticoids (49) could prevent anti-vector immune response if patient is seropositive for AAV2), Lower gene expression than SR |
| Potential target diseases and applications | Retinitis Pigmentosa: optogenetic vision restoration (Jaws) (4, 15) Achromatopsia: CNGA3 or CNGB3(47) | | | |

(NAbs: neutralizing antibodies; CGNA3: cyclic nucleotide gated channel alpha 3; CGNB3: cyclic nucleotide gated channel beta 3).

SEQUENCES

SEQ ID NO: 1: insertion peptide 7m8 without spacer
LGETTRP
SEQ ID NO: 2: insertion peptide
NETITRP
SEQ ID NO: 3: insertion peptide
KAGQANN
SEQ ID NO: 4: insertion peptide
KDPKTTN
SEQ ID NO: 5: insertion peptide
KDTDTTR
SEQ ID NO: 6: insertion peptide
RAGGSVG
SEQ ID NO: 7: insertion peptide
AVDTTKF
SEQ ID NO: 8: insertion peptide
STGKVPN
SEQ ID NO: 9: insertion peptide 7m8
AALGETTRPA
SEQ ID NO: 10: wild-type AAV9 VP1 capsid MAADGYLPDWLEDNLSEGIREWWALKPGAPQPKANQQHQDNARGLVLPG
YKYLGPGNGLDKGEPVNAADAAALEHDKAYDQQLKAGDNPYLKYNHADA
EFQERLKEDTSFGGNLGRAVFQAKKRLLEPLGLVEEAAKTAPGKKRPVE
QSPQEPDSSAGIGKSGAQPAKKRLNFGQTGDTESVPDPQPIGEPPAAPS
GVGSLTMASGGGAPVADNNEGADGVGSSSGNWHCDSQWLGDRVITTSTR
TWALPTYNNHLYKQISNSTSGGSSNDNAYFGYSTPWGYFDFNRFHCHFS
PRDWQRLINNNWGFRPKRLNFKLFNIQVKEVTDNNGVKTIANNLTSTVQ
VFTDSDYQLPYVLGSAHEGCLPPFPADVFMIPQYGYLTLNDGSQAVGRS
SFYCLEYFPSQMLRTGNNFQFSYEFENVPFHSSYAHSQSLDRLMNPLID
QYLYYLSKTINGSGQNQQTLKFSVAGPSNMAVQGRNYIPGPSYRQQRVS
TTVTQNNNSEFAWPGASSWALNGRNSLMNPGPAMASHKEGEDRFFPLSG
SLIFGKQGTGRDNVDADKVMITNEEEIKTTNPVATESYGQVATNHQSAQ
QAQTGWVQNQGILPGMVWQDRDVYLQGPIWAKIPHTDGNFHPSPLMGGF
GMKHPPPQILIKNTPVPADPPTAFNKDKLNSFITQYSTGQVSVEIEWEL
QKENSKRWNPEIQYTSNYYKSNNVEFAVNTEGVYSEPRPIGTRYLTR SEQ ID NO: 11: VP1 capsid of the recombinant AAV9-derived vector MAADGYLPDWLEDNLSEGIREWWALKPGAPQPKANQQHQDNARGLVLPG
YKYLGPGNGLDKGEPVNAADAAALEHDKAYDQQLKAGDNPYLKYNHADA
EFQERLKEDTSFGGNLGRAVFQAKKRLLEPLGLVEEAAKTAPGKKRPVE
QSPQEPDSSAGIGKSGAQPAKKRLNFGQTGDTESVPDPQPIGEPPAAPS
GVGSLTMASGGGAPVADNNEGADGVGSSSGNWHCDSQWLGDRVITTSTR
PRDWQRLINNNWGFRPKRLNFKLFNIQVKEVTDNNGTWALPTYNNHLYK
QISNSTSGGSSNDNAYFGYSTPWGYFDFNRFHCHFSVKTIANNLTSTVQ
VFTDSDYQLPYVLGSAHEGCLPPFPADVFMIPQYGYLTLNDGSQAVGRS
SFYCLEYFPSQMLRTGNNFQFSYEFENVPFHSSYAHSQSLDRLMNPLID
QYLYYLSKTINGSGQNQQTLKFSVAGPSNMAVQGRNYIPGPSYRQQRVS
TTVTQNNNSEFAWPGASSWALNGRNSLMNPGPAMASHKEGEDRFFPLSG
SLIFGKQGTGRDNVDADKVMITNEEEIKTTNPVATESYGQVATNHQSAQ
AALGETTRPAQAQTGWVQNQGILPGMVWQDRDVYLQGPIWAKIPHTDGN
FHPSPLMGGFGMKHPPPQILIKNTPVPADPPTAFNKDKLNSFITQYSTG
QVSVEIEWELQKENSKRWNPEIQYTSNYYKSNNVEFAVNTEGVYSEPRP
IGTRYLTR SEQ ID NO: 12: pR1.7 promoter ggaggctgaggggtggggaaagggcatgggtgtttcatgaggacagagc
ttccgtttcatgcaatgaaaagagtttggagacggatggtggtgactgg -continued

```
actatacacttacacacggtagcgatggtacactttgtattatgtatat
tttaccacgatcttttaaagtgtcaaaggcaaatggccaaatggttcc
ttgtcctatagctgtagcagccatcggctgttagtgacaaagccctga
gtcaagatgacagcagccccataactcctaatcggctctcccgcgtgg
agtcatttaggagtagtcgcattagagacaagtccaacatctaatcttc
caccctggccagggcccagctggcagcgagggtgggagactccgggca
gagcagagggcgctgacattggggcccggcctggcttgggtccctctgg
cctttcccaggggccctcttcttggggctttcttgggccgccactg
ctcccgctcctctcccccatcccacccctcaccccctcgttcttcat
atccttctctagtgctccctccactttcatccaccttctgcaagagtg
tgggaccacaaatgagttttcacctggcctggggacacacgtgccccca
caggtgctgagtgactttctaggacagtaatctgctttaggctaaaatg
ggacttgatcttctgttagccctaatcatcaattagcagagccggtgaa
ggtgcagaacctaccgcctttccaggcctcctcccacctctgccacctc
cactctccttcctgggatgtgggggctggcacacgtgtgcccagggca
ttggtgggattgcactgagctgggtcattagcgtaatcctggacaaggg
cagacagggcgagcggagggccagctccggggctcaggcaaggctgggg
gcttccccagacaccccactcctcctctgctggaccccacttcatag
ggcacttcgtgttctcaaagggcttccaaatagcatggtggccttggat
gcccagggaagcctcagagttgcttatctccctctagacagaagggaa
tctcggtcaagagggagaggtcgccctgttcaaggccacccagccagct
catggcggtaatgggacaaggctggccagccatcccaccctcagaaggg
acccggtggggcaggtgatctcagaggaggctcacttctgggtctcaca
ttcttggatccggttccaggcctcggccctaaatagtctccctgggctt
tcaagagaaccacatgagaaaggaggattcgggctctgagcagtttcac
cacccaccccccagtctgcaaatcctgacccgtgggtccacctgccca
aaggcggacgcaggacagtagaagggaacagagaacacataaacacaga
gagggccacagcggctcccacagtcaccgccaccttcctggcggggatg
ggtggggcgtctgagtttggttcccagcaaatccctctgagccgcctt
gcgggctcgcctcaggagcaggggagcaagaggtgggaggaggaggtct
aagtccaggccaattaagagatcaggtagtgtagggtttgggagctt
ttaaggtgaagaggcccggctgatcccacaggccagtataaagcgccg
tgaccctcaggtgatgcgccagggccggctgccgtcggggacagggctt
tccatagcc
```

SEQ ID NO: 13: Jaws-GFP=Halo57+2 mutations+KGC+GFP+ER2

```
MTAVSTTATTVLQATQSDVLQEIQSNFLLNSSIWVNIALAGVVILLFVA
MGRDLESPRAKLIWVATMLVPLVSISSYAGLASGLTVGFLQMPPGHALA
GQEVLSPWGRYLTWTFSTPMILLALGLLADTDIASLFTAITMDIGMCVT
GLAAALITSSHLLRWVFYGISCAFFVAVLYVLLVQWPADAEAAGTSEIF
GTLRILTVVLWLGYPILFALGSEGVALLSVGVTSWGYSGLDILAKYVFA
FLLLRWVAANEGTVSGSGMGIGSGGAAPADDRPVVKSRITSEGEYIPLD
QIDINVAPAGAVSKGEELFTGVVPILVELDGDVNGHKFSVSGEGEGDAT
YGKLTLKFICTTGKLPVPWPTLVTTLTYGVQCFSRYPDHMKQHDFFKSA
MPEGYVQERTIFFKDDGNYKTRAEVKFEGDTLVNRIELKGIDFKEDGNI
LGHKLEYNYNSHNVYIMADKQKNGIKVNFKIRHNIEDGSVQLADHYQQN
TPIGDGPVLLPDNHYLSTQSALSKDPNEKRDHMVLLEFVTAAGITLGMD
ELYKVAFCYENEV
```

SEQ ID NO: 14: Jaws=Halo57+2 mutations+KGC+ER2

```
MTAVSTTATTVLQATQSDVLQEIQSNFLLNSSIWVNIALAGVVILLFVA
MGRDLESPRAKLIWVATMLVPLVSISSYAGLASGLTVGFLQMPPGHALA
GQEVLSPWGRYLTWTFSTPMILLALGLLADTDIASLFTAITMDIGMCVT
GLAAALITSSHLLRWVFYGISCAFFVAVLYVLLVQWPADAEAAGTSEIF
GTLRILTVVLWLGYPILFALGSEGVALLSVGVTSWGYSGLDILAKYVFA
FLLLRWVAANEGTVSGSGMGIGSGGAAPADDRPVVKSRITSEGEYIPLD
QIDINVAPAGAVAFCYENEV
```

SEQ ID NO: 15: Halo57+2 mutations+KGC

```
MTAVSTTATTVLQATQSDVLQEIQSNFLLNSSIWVNIALAGVVILLFVA
MGRDLESPRAKLIWVATMLVPLVSISSYAGLASGLTVGFLQMPPGHALA
GQEVLSPWGRYLTWTFSTPMILLALGLLADTDIASLFTAITMDIGMCVT
GLAAALITSSHLLRWVFYGISCAFFVAVLYVLLVQWPADAEAAGTSEIF
GTLRILTVVLWLGYPILFALGSEGVALLSVGVTSWGYSGLDILAKYVFA
FLLLRWVAANEGTVSGSGMGIGSGGAAPADDRPVVKSRITSEGEYIPLD
QIDINV
```

REFERENCES

Throughout this application, various references describe the state of the art to which this invention pertains. The disclosures of these references are hereby incorporated by reference into the present disclosure.

1. Wässle H, Grunert U, Röhrenbeck J, Boycott B B. Cortical magnification factor and the ganglion cell density of the primate retina. *Nature* 1989; 341(6243):643-646.
2. Kolb H, Zhang L, Dekorver L, Cuenca N. A new look at calretinin-immunoreactive amacrine cell types in the monkey retina. *J. Comp. Neurol.* 2002; 453(2):168-84.
3. Wikler K C, Williams R W, Rakic P. Photoreceptor mosaic: Number and distribution of rods and cones in the rhesus monkey retina. *J. Comp. Neurol.* 1990; 297(4): 499-508.
4. Busskamp V et al. Genetic reactivation of cone photoreceptors restores visual responses in retinitis pigmentosa. [Internet]. *Science* 2010; 329(5990):413-7.
5. Byrne L C et al. Viral-mediated RdCVF and RdCVFL expression protects cone and rod photoreceptors in retinal degeneration. [Internet]. *J. Clin. Invest.* 2015; 125(1):105-16.

6. Komáromy A M et al. Gene therapy rescues cone function in congenital achromatopsia. *Hum. Mol. Genet.* 2010; 19:2581-2593.
7. Maguire A M et al. Safety and Efficacy of Gene Transfer for Leber's Congenital Amaurosis. *N. Engl. J. Med.* 2008; 358(21):2240-2248.
8. Bainbridge J W B et al. Effect of gene therapy on visual function in Leber's congenital amaurosis. *N. Engl. J. Med.* 2008; 358(21):2231-9.
9. Cideciyan A V et al. Human gene therapy for RPE65 isomerase deficiency activates the retinoid cycle of vision but with slow rod kinetics. *Proc. Natl. Acad. Sci. U.S.A.* 2008; 105(39):15112-7.
10. Bainbridge J W B et al. Long-Term Effect of Gene Therapy on Leber's Congenital Amaurosis. *N. Engl. J. Med.* 2015; 150504083137004.
11. Jacobson S G et al. Improvement and Decline in Vision with Gene Therapy in Childhood Blindness. *N Engl. J. Med.* 2015; 150503141523009.
12. Jacobson S G et al. Gene therapy for leber congenital amaurosis caused by RPE65 mutations: safety and efficacy in 15 children and adults followed up to 3 years. *Arch. Ophthalmol.* 2012; 130(1): 9-24.
13. MacLaren R E et al. Retinal gene therapy in patients with choroideremia: Initial findings from a phase 1/2 clinical trial. *Lancet* 2014; 383(9923):1129-1137.
14. Duncan J L. Visual Consequences of Delivering Therapies to the Subretinal Space. *JAMA Ophthalmol.* 2017; 135(3): 242-243. doi:10.1001/jamaophthalmol.2016.5659.
15. Chuong A S et al. Noninvasive optical inhibition with a red-shifted microbial rhodopsin [Internet]. *Nat Neurosci* 2014; 17(8): 1123-1129.
16. Dalkara D et al. In Vivo-Directed Evolution of a New Adeno-Associated Virus for Therapeutic Outer Retinal Gene Delivery from the Vitreous. *Sci. Transl. Med.* 2013; 5(189):189ra76-189ra76.
17. Khabou H et al. Insight into the mechanisms of enhanced retinal transduction by the engineered AAV2 capsid variant −7m8. *Biotechnol. Bioeng.* [published online ahead of print: June 2016]; doi:10.1002/bit.26031.
18. Ye G-J et al. Cone-Specific Promoters for Gene Therapy of Achromatopsia and Other Retinal Diseases. *Hum. Gene Ther.* 2016; 27(1):72-82.
19. Ye G et al. Safety and Biodistribution Evaluation in CNGB3-Deficient Mice of rAAV2tYF-PR1. 7-hCNGB3, a Recombinant AAV Vector for Treatment of Achromatopsia2016; 27(1):27-37.
20. Kolstad K D et al. Changes in adeno-associated virus-mediated gene delivery in retinal degeneration. *Hum. Gene Ther.* 2010; 21(5):571-578.
21. Vacca O et al. AAV-mediated gene delivery in Dp71-null mouse model with compromised barriers. [Internet]. *Glia* 2014; 62(3):468-76.
22. Satoh S et al. The spatial patterning of mouse cone opsin expression is regulated by bone morphogenetic protein signaling through downstream effector COUP-TF nuclear receptors. *J. Neurosci.* 2009; 29(40): 12401-11.
23. Pickrell S W, Zhu X, Wang X, Craft C M. Deciphering the contribution of known cis-elements in the mouse cone arrestin gene to its cone-specific expression. *Investig. Ophthalmol. Vis. Sci.* 2004; 45(11):3877-3884.
24. von Mering C et al. STRING 7—Recent developments in the integration and prediction of protein interactions. *Nucleic Acids Res.* 2007; 35(SUPPL. 1):358-362.
25. Blazek E, Mittler G, Meisterernst M. The mediator of RNA polymerase II. *Chromosoma* 2005; 113(8):399-408.
26. Regulators L T. Letter to the Editor A Unified Nomenclature for Protein Subunits of Mediator Complexes. *Mol. Cell* 2004; 14:553-557.
27. Boyd J M, Verma S, Uhlmann E. 14584 Corrections. *Annu. Rev. Microbiol.* 1998; 95:2-3.
28. Viets K, Eldred K C, Jr R J J. Mechanisms of Photoreceptor Patterning in Vertebrates and Invertebrates. *Trends Genet.* 2016; 32(10):638-659.
29. Ramachandran P S et al. Evaluation of Dose and Safety of AAV7m8 and AAV8BP2 in the Non-Human Primate Retina. *Hum. Gene Ther.* [published online ahead of print: October 2016]; doi:10.1089/hum.2016.111.
30. Vandenberghe L H et al. AAV9 targets cone photoreceptors in the nonhuman primate retina. *PLoS One* 2013; 8(1):e53463.
31. Vandenberghe L H et al. Dosage thresholds for AAV2 and AAV8 photoreceptor gene therapy in monkey. *Sci. Transl. Med.* 2011; 3(88):88ra54.
32. Kotterman M a et al. Antibody neutralization poses a barrier to intravitreal adeno-associated viral vector gene delivery to non-human primates. *Gene Ther.* 2014(August):1-11.
33. Sengupta A et al. Red-shifted channelrhodopsin stimulation restores light responses in blind mice, macaque retina, and human retina. *EMBO Mol Med* 2016; 1-17.
34. Bell C L, Gurda B L, Van Vliet K, Agbandje-McKenna M, Wilson J M. Identification of the Galactose Binding Domain of the Adeno-Associated Virus Serotype 9 Capsid. *J. Virol.* 2012; 86(13):7326-7333.
35. Dalkara D et al. In vivo-directed evolution of a new adeno-associated virus for therapeutic outer retinal gene delivery from the vitreous. [Internet]. *Sci. Transl. Med.* 2013; 5:189ra76.
36. Yin L et al. Intravitreal injection of AAV2 transduces macaque inner retina. *Invest. Ophthalmol. Vis. Sci.* 2011; 52(5):2775-83.
37. Reichman S, Terray A, Slembrouck A, Nanteau C, Orieux G. From confluent human iPS cells to self-forming neural retina and retinal pigmented epithelium[published online ahead of print: 2014]; doi:10.1073/pnas.1324212111.
38. Fradot M, Busskamp V, Bennett J. Gene Therapy in Ophthalmology: Validation on Cultured2011; 593(May): 587-593.
39. Sinha R et al. Cellular and Circuit Mechanisms Shaping the Perceptual Properties of the Primate Fovea. *Cell* 2017; 168(3):413-426.e12.
40. Anderson D H, Fisher S K. The relationship of primate foveal cones to the pigment epithelium. *J. Ultrastruct. Res.* 1979; 67(1):23-32.
41. Allocca M et al. Novel adeno-associated virus serotypes efficiently transduce murine photoreceptors. *J. Virol.* 2007; 81(20): 11372-80.
42. Kay C N et al. Targeting photoreceptors via intravitreal delivery using novel, capsid-mutated AAV vectors. *PLoS One* 2013; 8(4):e62097.
43. Jacobson S G et al. Gene Therapy for Leber Congenital Amaurosis caused by RPE65 mutations: Safety and Efficacy in Fifteen Children and Adults Followed up to Three Years. *Arch. Ophthalmol.* 2012; 130(1): 9-24.
44. Tenenbaum L, Lehtonen E, Monahan P E. Evaluation of risks related to the use of adeno-associated virus-based vectors. *Curr. Gene Ther.* 2003; 3(6):545-65.

45. Boyd R F et al. Photoreceptor-targeted gene delivery using intravitreally administered AAV vectors in dogs. *Gene Ther.* 2016; 23(2):223-230.

46. Ye G-J et al. Safety and Biodistribution Evaluation in Cynomolgus Macaques of rAAV2tYF-PR1.7-hCNGB3, a Recombinant AAV Vector for Treatment of Achromatopsia. *Hum. Gene Ther.* Clin. Dev. 2016; 27(1): hum.2015.164.

47. Maguire A M et al. Safety and efficacy of gene transfer for Leber's congenital amaurosis. *N. Engl. J. Med.* 2008; 358(21):2240-8.

48. Gernoux G, Wilson J M, Mueller C. Regulatory and Exhausted T Cell Responses to AAV Capsid. *Hum. Gene Ther.* 2017; 28(4):338-349.

49. Choi V W, Asokan A, Haberman R a, Samulski R J. Production of recombinant adeno-associated viral vectors. *Curr. Protoc. Hum. Genet.* 2007; Chapter 12:Unit 12.9.

50. Aurnhammer C et al. Universal real-time PCR for the detection and quantification of adeno-associated virus serotype 2-derived inverted terminal repeat sequences. *Hum. Gene Ther. Methods* 2012; 23(1):18-28.

51. Delyfer M-N et al. Transcriptomic Analysis of Human Retinal Detachment Reveals Both Inflammatory Response and Photoreceptor Death. *PLoS One* 2011; 6(12):e28791.

52. Reichman S et al. The homeobox gene CHX10NSX2 regulates RdCVF promoter activity in the inner retina. *Hum. Mol. Genet.* 2010; 19(2):250-61.

The invention claimed is:

1. A recombinant AAV9-derived vector, comprising:
a VP1 capsid protein comprising SEQ ID NO: 11; and
a polynucleotide of interest under the control of the pR1.7 promoter as set forth in SEQ ID NO: 12.

2. The recombinant AAV9-derived vector according to claim 1, wherein the polynucleotide of interest is a gene encoding retinitis pigmentosa GTPase regulator (RPGRORF15), CNGB3 (beta subunit of the cone cyclic nucleotide-gated cation channel), CNGA3 (alpha subunit of the cone cyclic nucleotide-gated cation channel) or GNAT2.

3. The recombinant AAV9-derived vector according to claim 1, wherein the polynucleotide of interest encodes a neurotrophic factor.

4. The recombinant AAV9-derived vector according to claim 1, wherein the polynucleotide of interest encodes RdCVF, RdCVF2, RdCVFL or RdCVFL2.

5. The recombinant AAV9-derived vector according to claim 1, wherein the polynucleotide of interest encodes an opsin.

6. The recombinant AAV9-derived vector according to claim 1, wherein the polynucleotide of interest encodes for an opsin consisting of SEQ ID NO: 13, SEQ ID NO: 14 or SEQ ID NO: 15.

7. The recombinant AAV9-derived vector according to claim 1, wherein the polynucleotide of interest encodes a site-specific endonuclease that provides for site-specific knock-down of gene function selected from the group consisting of zinc finger nucleases (ZFNs), transcription activator-like effector nucleases (TALENs), and CRISPR-associated endonucleases.

* * * * *